(12) United States Patent
Minutoli

(10) Patent No.: US 12,376,941 B2
(45) Date of Patent: Aug. 5, 2025

(54) INSERT ASSEMBLY WITH RADIOFREQUENCY IDENTIFIER FOR MEDICAL DEVICE

(71) Applicant: MECTRON S.P.A., Carasco (IT)

(72) Inventor: Saverio Minutoli, Carasco (IT)

(73) Assignee: Mectron S.p.A., Carasco (IT)

( * ) Notice: Subject to any disclaimer, the term of this patent is extended or adjusted under 35 U.S.C. 154(b) by 850 days.

(21) Appl. No.: 17/634,014

(22) PCT Filed: Aug. 6, 2020

(86) PCT No.: PCT/IB2020/057437
§ 371 (c)(1),
(2) Date: Feb. 9, 2022

(87) PCT Pub. No.: WO2021/028792
PCT Pub. Date: Feb. 18, 2021

(65) Prior Publication Data
US 2022/0313383 A1    Oct. 6, 2022

(30) Foreign Application Priority Data

Aug. 9, 2019  (IT) .................. 102019000014559

(51) Int. Cl.
*A61B 90/98*  (2016.01)
*A61B 90/00*  (2016.01)

(52) U.S. Cl.
CPC .............. *A61B 90/98* (2016.02); *A61B 90/08* (2016.02); *A61B 2090/0807* (2016.02); *A61B 2560/0406* (2013.01); *A61B 2560/0431* (2013.01)

(58) Field of Classification Search
None
See application file for complete search history.

(56) References Cited

U.S. PATENT DOCUMENTS

| | | | |
|---|---|---|---|
| 6,402,769 | B1 | 6/2002 | Boukhny |
| 7,374,552 | B2 | 5/2008 | Wuchinich |

(Continued)

FOREIGN PATENT DOCUMENTS

| | | |
|---|---|---|
| BR | 112020021887 A2 | 1/2021 |
| CN | 101807243 A | 8/2010 |

(Continued)

OTHER PUBLICATIONS

European Patent Office, International Search Report, issued in PCT/IB2020/057437, mailed Oct. 15, 2020, Rijswijk, NL.

(Continued)

*Primary Examiner* — Carlos Garcia
(74) *Attorney, Agent, or Firm* — Jason H. Foster; Kremblas & Foster

(57) ABSTRACT

An insert assembly, insertable in a handpiece of a medical device, has an insert having an insert metal tang, a ferromagnetic layer in contact with the insert metal tang, a dielectric layer in contact with the ferromagnetic layer, an insert antenna in contact with the dielectric layer, having an insert antenna metal element and configured to receive and transmit electromagnetic fields, and an identification chip operatively connected to the insert antenna and configured to transmit information about the insert assembly. The ferromagnetic layer reduces or cancels attenuation and/or distortion phenomena of an electromagnetic field caused by parasitic effects due to interaction of a transmitted or received electromagnetic field with metal parts of the insert metal tang, liquids present in the insert, and the insert antenna metal element. The ferromagnetic layer dielectric layer and insert antenna form a transceiver device putting the identification chip in communication with a handpiece antenna.

20 Claims, 19 Drawing Sheets

(56) References Cited

U.S. PATENT DOCUMENTS

| | | | |
|---|---|---|---|
| 10,893,883 B2 | 1/2021 | Dannaher | |
| 12,011,324 B2 * | 6/2024 | Minutoli | A61C 17/18 |
| 2002/0129454 A1 | 9/2002 | Hilscher et al. | |
| 2005/0083203 A1 | 4/2005 | Surkau | |
| 2008/0044790 A1 | 2/2008 | Fani et al. | |
| 2008/0293008 A1 | 11/2008 | Regere et al. | |
| 2009/0047624 A1 | 2/2009 | Tsai | |
| 2009/0065565 A1 | 3/2009 | Cao | |
| 2009/0236938 A1 | 9/2009 | Bromfield | |
| 2011/0087605 A1 | 4/2011 | Pond | |
| 2011/0278988 A1 | 11/2011 | Young et al. | |
| 2013/0253559 A1 | 9/2013 | Slipszenko et al. | |
| 2015/0147718 A1 | 5/2015 | Khakpour et al. | |
| 2015/0150647 A1 | 6/2015 | Chevalier | |
| 2018/0092712 A1 | 4/2018 | Bosisio | |
| 2018/0256287 A1 | 9/2018 | Bosisio et al. | |
| 2021/0219991 A1 | 7/2021 | Cerisola et al. | |
| 2022/0287798 A1 | 9/2022 | Minutoli | |
| 2022/0313383 A1 | 10/2022 | Minutoli | |

FOREIGN PATENT DOCUMENTS

| | | |
|---|---|---|
| CN | 112236240 A | 1/2021 |
| CN | 112236240 B | 5/2022 |
| DE | 10204884 A1 | 8/2003 |
| DE | 102005044074 A1 | 3/2007 |
| DE | 102017223191 A1 | 6/2019 |
| EP | 1531750 A1 | 5/2005 |
| EP | 2057960 B1 | 3/2018 |
| ES | 2913850 T3 | 6/2022 |
| JP | H0373207 A | 3/1991 |
| JP | 2021522045 A | 8/2021 |
| KR | 20210016524 A | 2/2021 |
| WO | 2006082340 A1 | 8/2006 |
| WO | 2014006579 A2 | 1/2014 |
| WO | 2018169565 A1 | 9/2018 |
| WO | 2021028764 A1 | 2/2021 |

OTHER PUBLICATIONS

Watanabe Y. et al., A study on a new flexural-mode transducer-solid horn system and its application to ultrasonic plastic welding, Ultrasonics, 1996, pp. 235-238, vol. 34, Elsevier Science B.V., NL.

Yun C-H. et al., A High Power Ultrasonic Linear Motor using a Longitudinal and Bending Hybrid Bolt-Clamped Langevin Type Transducer, Japanese Journal of Applied Physics, 2001, pp. 3773-3776, vol. 40, No. 5S, ©The Japan Society of Applied Physics, IOP Publishing, JP.

* cited by examiner

INSERT ASSEMBLY WITH RADIOFREQUENCY IDENTIFIER FOR MEDICAL DEVICE

CROSS-REFERENCE TO RELATED APPLICATIONS

This application is a National Phase Application of PCT International Application No. PCT/IB2020/057437, having an International Filing Date of Aug. 6, 2020 which claims the benefit of priority to Italian Patent Application No. 102019000014559, filed Aug. 9, 2019, each of which is hereby incorporated by reference in its entirety.

FIELD OF THE INVENTION

The present invention relates to an insert assembly with radiofrequency identifier for medical device.

In particular, the present invention relates to an insert assembly comprising an insert and a radiofrequency identifier, said insert assembly being adapted to be inserted in a medical device handpiece, in which said insert is adapted to interact with a part of the patient's body.

Furthermore, the present invention relates to a handpiece assembly for ultrasonic piezoelectric devices adapted to recognize inserts by using a miniaturized radiofrequency identifier.

Furthermore, the present invention relates to the context of an ultrasonic system which is particularly and advantageously applied in the medical-surgical field (e.g., neuro-spinal, craniofacial, orthopedic, otorhinolaryngological), in dental, surgical and non-surgical fields (e.g., oral surgery, implantology, dental hygiene, and prophylaxis, etc.) but which is equally usable in the industrial or construction field according to other embodiments.

More precisely, such a system can be used in fields in which it is necessary to perform a removal, abrasion, cutting or drilling of material, e.g., mineralized material.

Hereinafter, application will mean application in the medical-surgical field (e.g., neuro-spinal, craniofacial, orthopedic, otorhinolaryngological), dental field, surgical and non-surgical field (e.g., in oral surgery, implantology, dental hygiene, and prophylaxis, etc.) but it is equally usable in the industrial or construction field according to other embodiments, fields in which it is necessary to perform a removal, abrasion, cutting or drilling of material, e.g., mineralized type, such as bone, enamel, dentin, dental calculus, and biofilm.

BACKGROUND OF THE INVENTION

In the medical or dental field, and specifically in the surgical or implantology field, power ultrasounds are applied in the dissection of hard tissues (bone) and soft tissues, in the cauterization of blood vessels and in the field of dental prophylaxis for the removal of tartar.

Referring to the field of implantology merely by way of example, the sites for the insertion of screws or other fixing systems into the bone are prepared by using rotating tools of the aforementioned type, which however have serious limitations both intra-surgery for the operator and post-surgery for the patient.

Just to mention a few, the traditional instruments are problematic when operating on surgical sites in the presence of complex anatomical structures of difficult or limited surgical access, or near delicate anatomical structures, such as nerves and blood vessels.

The large amount of mechanical energy produced by the rotation and the considerable pressure that the operator must apply onto the instrument are responsible for possible damage to non-mineralized structures, for the production of a considerable amount of heat, for losses due to friction, with a consequent overheating of the mineralized tissues, for operator fatigue at the expense of the required intra-surgery precision and control.

The context of the present invention relates to ultrasonic power systems for medical and dental use, e.g., such as oral implantology. However, this invention can be equally applied to other fields of the medical and industrial fields.

The operation of most ultrasonic power systems is based on the transmission of longitudinal waves in the application means. Such waves are generated by piezoelectric transducers and transferred into the means through concentrators or waveguides referred to as ultrasonic horns.

However, there are applications in which flexural, torsional, or compound vibrations are used. In the dental field, for example, longitudinal vibrations excited in the ultrasound transducers are converted into flexural oscillations through asymmetrically shaped tips or inserts. The incorporation of one or more curves in the insert profile has a dual purpose, i.e., to allow a good access to the inside of the oral cavity and to convert the longitudinal movement of the transducer into a linear flexural vibration close to the operating part of the insert.

In ultrasound ablators, the flexural movement of hooked-shaped inserts is normally used to remove calcified deposits (tartar) from teeth. In ultrasound scalpels (such as the "Piezosurgery device" from Mectron S.p.A.) the transversal movement produced in scythe-shaped inserts is used to dissect mandibular bones and other mineralized tissues with precision.

There are also ultrasonic ablators which remove tartar through both linear and elliptical oscillations, as described in DE102005044074A1 or in EP2057960B1. In these systems, vibratory movements having bidirectional components are generated in the inserts by flexural vibrations of the transducer on orthogonal planes, see in particular EP2057960B1. The configurations of these flexural transducers refer to a previously disclosed concept in which transverse oscillation is caused by adjacent piezoelectric volumes inserted radially and axially with opposite polarizations [see Mori, E. et al., "*New Bolt Clamped Flexural Mode Ultrasonic High Power Transducer with One-Dimensional Construction*", Ultrasonics International 89 Conference Proceedings"; Watanabe, Y. et al., "*A Study on a New Flexural-mode Transducer-solid Horn System and its Application to Ultrasonic Plastic Welding*", Ultrasonics Vol. 34, 1996, pp. 235-238; Yun, C-H. et al "*A High Power Ultrasonic Linear Motor using a Longitudinal and Bending Hybrid Bolt-Clamped Langevin Type Transducer*", Jpn. J. Appl. Phys., Vol. 40, 2001, pp. 3773-3776].

In maxillofacial surgery procedures, the ultrasonic oscillations of the inserts are commonly used to sever bone tissue.

According to dental implantology protocol, once the first hole of reduced size has been obtained, it is progressively enlarged using rotary drills of an increasing section until it reaches a diameter compatible with the implant.

The inserts typically used in ultrasound systems for operations performed in the oral cavity have insufficient oscillatory amplitudes to perform all the stages of implant site preparation. Such a limitation is inherent in the design of these devices in which the larger the sections of the inserts, the smaller the amplitude of the produced vibration, using the same handpiece. This inverse relation between the section and the oscillation of the inserts is a limit of applicability of the technology, especially in oral implantology in which drilling holes several millimeters in diameter is required.

There is a further problem related to the linear vibration of the inserts, which does not allow the perforation of the mandibular tissue unless a manual swing of the handpiece is applied in combination therewith. Such an auxiliary movement is certainly difficult to produce by the operator inside the mouth and is in any case not very compatible with the requirements of precision which clinical implantology practice requires today.

Ultrasonic devices adapted to dissect biological tissue by excitation of torsional or combined torsional and longitudinal ultrasonic vibrations have been known from U.S. Pat. No. 7,374,552B2, U.S. Pat. No. 6,402,769B1, US2009/236938A1, US2011/0278988A1. The common feature of these devices is that they all have a single geometric development axis, being basically axial-symmetrical systems. In maxillofacial applications, such as dental implantology, the oscillating inserts used in the oral cavity have significantly asymmetrical developments relative to the transducer axis. Therefore, in these fields it is not possible to produce torsional or longitudinal and torsional vibrations in the operating parts of the inserts following the teachings of the mentioned inventions (valid only for systems in which transducer and operating parts are coaxial).

Slipszenko (US2013/0253559A1) devised ultrasonic system configurations in which torsional, flexural, or longitudinal vibrations are alternately produced in ultrasonic scalpels for the treatment of soft tissues with a developmental axis perpendicular to that of the transducer. According to this solution, the transverse vibration of the piezoelectric transducer can be transformed into torsional, flexural, or longitudinal oscillation by incorporating an ultrasonic horn or waveguide mounted eccentrically with respect to the transducer axis. For the vibration transmission to take place correctly, the diameter of the back of the horn must be greater than that of the transducer. Although it is possible to generate alternative vibratory families on orthogonal planes, the specific requirements of compactness, ergonomics, and weight of dental and medical devices cannot be achieved by applying Slipszenko's solution. The large size and eccentric mounting of the ultrasonic horn would significantly limit visibility inside the oral cavity. Furthermore, in Slipszenko's solution, one or more waveguides are inserted between the scalpel and the conversion/vibratory transmission horn to transmit adequate vibrations. Even reducing the number of these components to a minimum, the overall length of the device would still be incompatible for applications in small, cramped, and delicate spaces, such as inside the oral or maxillofacial or neuro-spinal or skull cavity.

Mishiro (JPH0373207A) suggested an ultrasonic system for the removal of material which could theoretically find applicability in dental applications. The suggested solution is based on a typical operating principle of ultrasonic motors in which the elliptical vibration generated in a joint formed by an ultrasonic transducer coupled to a waveguide produces the rotation of an operating tool kept in contact with the tip of the waveguide. In the configurations disclosed in JPH0373207A, the operating tool, the axis of symmetry of which can be either perpendicular or parallel to that of the transducer, in addition to rotating, oscillates ultrasonically, allowing the removal of material. The contact point between the operating tool and the waveguide through which the oscillatory movement is transferred is generated by rotation and corresponds to an antinode of the longitudinal and transverse vibrations generated in the joint transducer-waveguide. According to the configurations described in this solution, the operating element is supported by two pads positioned at the same number of stationary nodes produced along the oscillating element. Such a solution appears complex in the implementation thereof and unsuitable for applications in which the operating tools (inserts) must be used and replaced in succession, as in dental implantology.

Furthermore, in the field of biomedical or medical instruments, the need for continuous improvement of patient safety is strongly felt.

For this reason, it must be guaranteed that inserts for biomedical instruments (e.g., insert tips adapted to operate on the teeth of a patient in a medical device for dental use or, for example, on bones in an instrument for surgical use in districts, such as the maxillofacial or neuro-spinal or skull or orthopedic district) always operate correctly and safely, come from reliable manufacturers, are of the right type for the medical device, have not been overused, and so on.

For this purpose, it is very important to have inserts equipped with an identifier, capable of providing information about the inserts and its operation to a control unit of the medical device.

In this regard, inserts provided with RFID identifiers are known, adapted to communicate wirelessly with the remaining part of the medical device.

Solutions of this type are described for example in WO2006082340, US2011087605A1, US2015147718A1, US2009047624A1, US2008044790A1, US2009065565A1, US2015150647A1.

However, because of the particular features of the inserts used in this field, above all the very small size and the presence of a metal element which forms the insert body, the communication performance provided by the known solutions is unsatisfactory with respect to needs or does not find applications available to users today.

More specifically, the miniature antennas arranged in the insert to ensure the wireless communication of the RFID identifier with the rest of the medical device, i.e., for the excitation of the RFID identifier, act like inductances.

However, such inductances are disturbed by the presence of the metal of the insert body, and further by possible liquids (e.g., physiological solutions which are saline by their nature) which may be present in the insert, which act as antagonists of the electromagnetic fields, because they tend to absorb the electro-magnetic fields and, in the case of metals, to re-emit the electro-magnetic fields symmetrically causing the cancellation thereof in the boundary zone of the metal.

In summary, the overall result of such phenomena is a strong attenuation, or even cancellation, of the signals carried by the electromagnetic fields in the vicinity of the insert antenna, which worsens the performance of the communication between the RFID identifier and the rest of the medical device or even prevents such communications from taking place. This situation actually frustrates the advantages of the RFID identifier.

A further drawback of the aforesaid known solutions of inserts with RFID identifiers consists of the difficulty in designing insert antennas operating at the frequencies required by UHF RFID communication, according to the different expected standards for this type of communication in various countries.

In summary, the need for medical instrument inserts provided with identifiers adapted to support effective and reliable communication with the remaining parts of the medical device remains unsatisfied.

Furthermore, it must be considered that the inserts must be interchangeably connected to ultrasonic generators and, to be used repeatedly, they must be able to be separated from the handpiece and placed in an autoclave, leading to repeated and very stressful treatment cycles for any RFID identifiers connected thereto.

Therefore, the need is still strongly felt for insert identification solutions which are not only small in size, and thus able to adapt to small distal portions of the handpiece, i.e., adapted to tight operating or intervention fields, but at the same time are very resistant to the stresses imposed by autoclaves or similar treatment cycles for the sterilization thereof.

The previously mentioned need to put the RFID identifier of the insert in wireless communication with the rest of the medical device places additional requirements on the medical device handpiece. Such a handpiece must be provided with a radiofrequency antenna, which must be appropriately powered.

The reading antenna positioned inside the handpiece must meet very stringent dimensional and operational requirements. The dimensions of the antenna must be miniaturized so that the antenna can be contained in the handpiece. This suggests using ring or loop antennas.

However, small ring or loop antennas suffer from several problems. One of the main problems arises from the fact that the currents circulating in the antenna ring, depending on the working frequency and geometric dimensions, tend to have so-called voids, i.e., points in which the current undergoes a phase inversion. Such a phenomenon means that the antenna emission is zero in some points, because the current is zero, and also causes other low emission points, in which the phase current is opposite to the primary one. Ultimately, this significantly worsens the transmission performance of the antenna.

A further fundamental need to minimize energy loss and generation of line reflections due to environmental electromagnetic spurious events derives from the need to ensure the adaptation of antenna impedance in the UHF frequency range to the generator in the medical device, which is not easy to achieve in this scope of application due to the small size of the antenna and available space.

Finally, the need arises to transmit the radiofrequency signals inside the handpiece intended to supply the handpiece antenna, under impedance adaptation conditions, and in the absence of radiofrequency connectors.

Therefore, the further need for effective radiofrequency signal transceiver solutions in the handpiece to allow effective wireless communication with the insert radiofrequency identifier is still strongly felt and currently not met.

German patent application DE 102 04 884 A1 describes a "label with transponder", or "RFID label" provided with a miniaturized oscillating circuit and antenna, not associated with use on a medical device, and operating at a frequency of 13.56 MHz.

SUMMARY OF THE INVENTION

It is the object of the present invention to provide a medical device insert assembly which allows to solve the drawbacks described above with reference to the background art and to respond to the aforesaid needs particularly felt in the technical field considered.

Such an object is achieved by an insert assembly as described and claimed herein.

Further embodiments of the insert assembly are also described.

It is a further object of the present invention to provide a medical device comprising the aforesaid insert assembly.

Such an object is achieved by a medical device as described and claimed herein.

A further embodiment of the medical device is also described.

Some of the main advantages arising from this invention are the following ones.

The position, thickness and type of materials allow to minimize the increase in diameter of the insert, without obstructing the clinician's vision of the surgical site, thus ensuring and maintaining the patient's safety.

The small dimensions and light weight of the materials and RFID chip, i.e., of the materials added to the metal of the insert, less than 15 grams, do not significantly affect the mechanical properties of the ultrasonic transducer when it is mechanically coupled to the insert, thus leaving the working parameters, such as ultrasonic frequency and amplitude and power of the device, unchanged, always ensuring the maximum and safe performance of the medical device.

The position, small dimensions, and weight of the materials and RFID chip on the insert prevent degradation and ensure that the insert maintains the lifetime, efficiency, and effectiveness thereof.

The position and the small increase in insert diameter do not affect the simplicity of mechanical coupling between insert and transducer by means of a torque wrench or instrument based on the dynamometric method.

The type of RFID system materials on the insert is suited to the temperatures used in the sterilization processes, such as autoclaves and/or instrument cleaners.

The type of RFID coating materials on the insert which interfaces with the patient is biocompatible.

The small number of layers of the RFID system on the insert ensures the simplicity of the production process, providing a system which is always highly efficient.

The reduced thickness of the RFID system and the consequent minimal increase of the diameter of the insert ensures an adequate concentric area free from the components surrounding the handpiece, ensuring that production process tolerances or flexure caused by excessive pressures imposed by the clinician during operations can put the mechanical parts of the transducer into contact with the insert causing variations in the working parameters of the device.

Identification of the insert by means of the unique, non-writable code of the RFID insert chip.

Identification of the handpiece or handpiece antenna by means of the unique, non-writable code of the RFID handpiece chip.

In particular for the patient's safety, the unique RFID identification, in conjunction with the medical device, allows:

a. secure traceability of the insert or handpiece, throughout the life cycle thereof
b. indication to the clinician that the insert and handpiece are adequate and compatible
c. indication to the clinician that the selected insert is adequate and suitable for the selected intervention type
d. indication to the clinician of the performance of the insert, having evaluated the chronology of the current and past manners and times of use e. instructions to the clinician on appropriate settings of the medical device concerning the insert in use
f. indications of clinical protocols and the respective steps of operation
g. predictive maintenance
h. scheduled maintenance
i. sharing data with the manufacturer for statistics and continuous improvement of products and the conditions of use thereof
j. sharing data with the manufacturer for updating medical devices and possible integrations of new products or usage models for greater efficiency and effectiveness of the medical system with insert
k. sharing data with universities, training centers, etc.
l. writing medical records and specifically history of the inserts used for patient treatments.

Easy cleaning and sterilization of all RFID systems, both of the insert and of the distal antenna handpiece position and the handpiece and cable joining the medical device to the handpiece, according to the usual clinical protocols.

In some implementations, the possibility of extracting the antenna handpiece for maintenance as well as for cleaning and sterilization.

The data transmission channel of the RFID system shares, where present, the connections for the illumination of the handpiece cone in the distal position, with the benefit of not increasing the possible anomalies due to more connections and wires, and maintaining the flexibility of the cable joining the medical device to the handpiece.

Therefore, the present invention provides a universal solution applicable both in dental surgery and prophylaxis or maxillofacial surgery or orthopedics or neuro-spinal or otorhinolaryngological or craniofacial surgery, and in other fields in medical and industrial fields.

BRIEF DESCRIPTION OF THE DRAWINGS

Further features and advantages of the handpiece for medical device according to the invention will be apparent from the following description of preferred embodiments, given by way of indicative, non-limiting examples, with reference to the accompanying figures, in which.

DETAILED DESCRIPTION

The term "miniaturized" means a device or component having a size between 50 micrometers and 800 micrometers, preferably between 100 micrometers and 600 micrometers.

The term "medical device" means an electromechanical device in which a piezoelectric handpiece actuates the mechanical movement of ultrasonic frequency inserts. These devices can be applied in several fields, of which the following are listed as examples only:

medical: in particular, surgery in the neuro-spinal, cranio-maxillofacial, orthopedic, otorhinolaryngological, pediatric disciplines;

dental, and in particular, surgery, dentistry in general, hygiene and prophylaxis (in particular, the removal of dental calculi, plaque, and biofilm).

The function carried out by the device on bone or on tooth means, for example:
cutting;
perforating;
removing;
eroding.

The function performed by the device on calculi/plaque/biofilm means, for example:
removing;
disintegrating.

Figure 1:
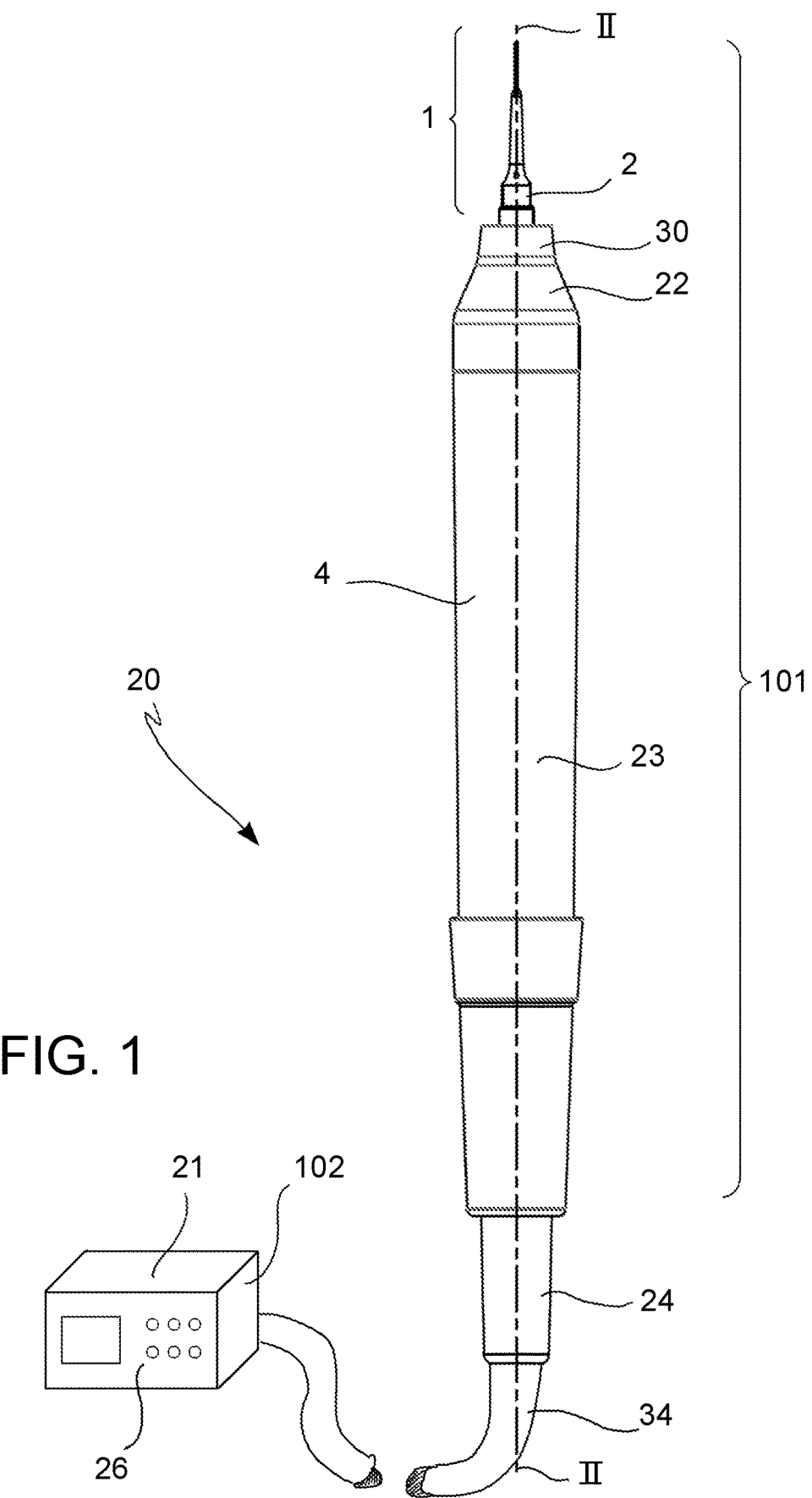
FIG. 1 shows a diagrammatic assembly view of a medical device comprising an ultrasonic system with excitation handpiece and an interchangeable insert assembly, e.g. for dental or microsurgical use.
Figure 2:
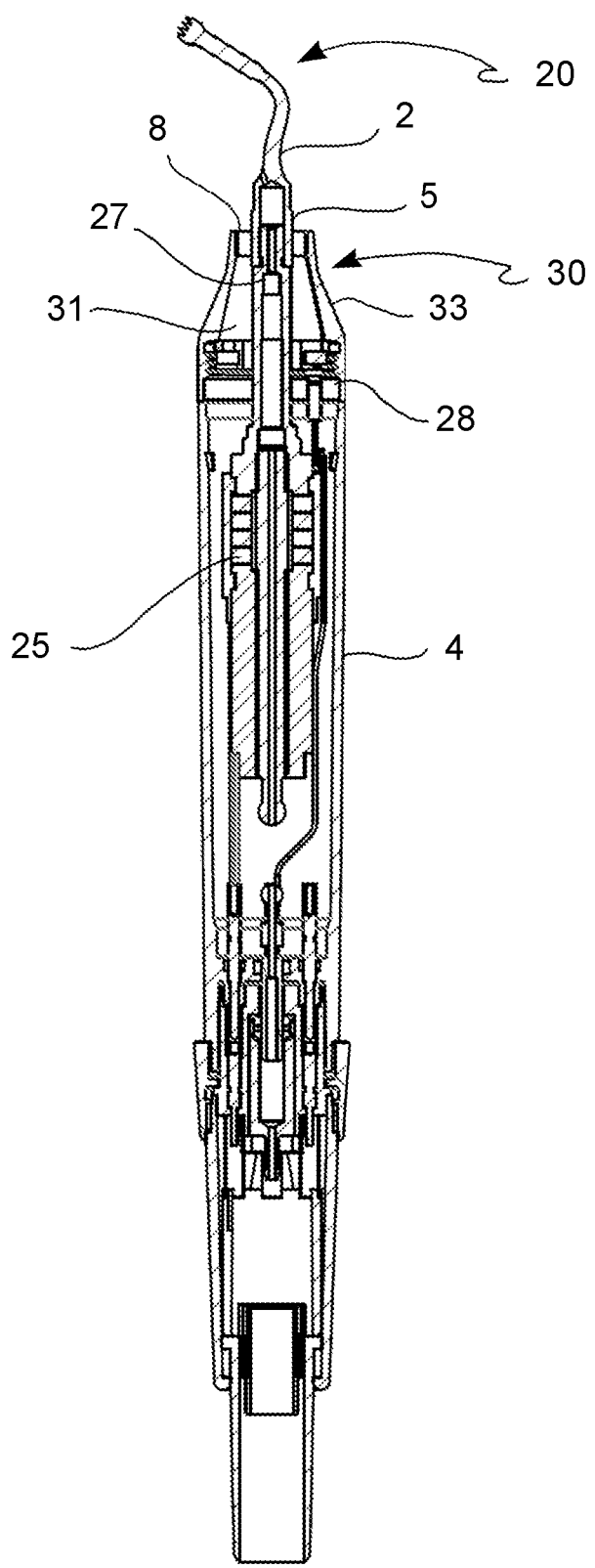
FIG. 2 shows a section view taken along line II-II of FIG. 1 of the particular of the handpiece assembly and insert assembly of FIG. 1, in which the components of the handpiece, such as a transducer, e.g. a piezoelectric transducer, are highlighted.
Figures 3, 4:
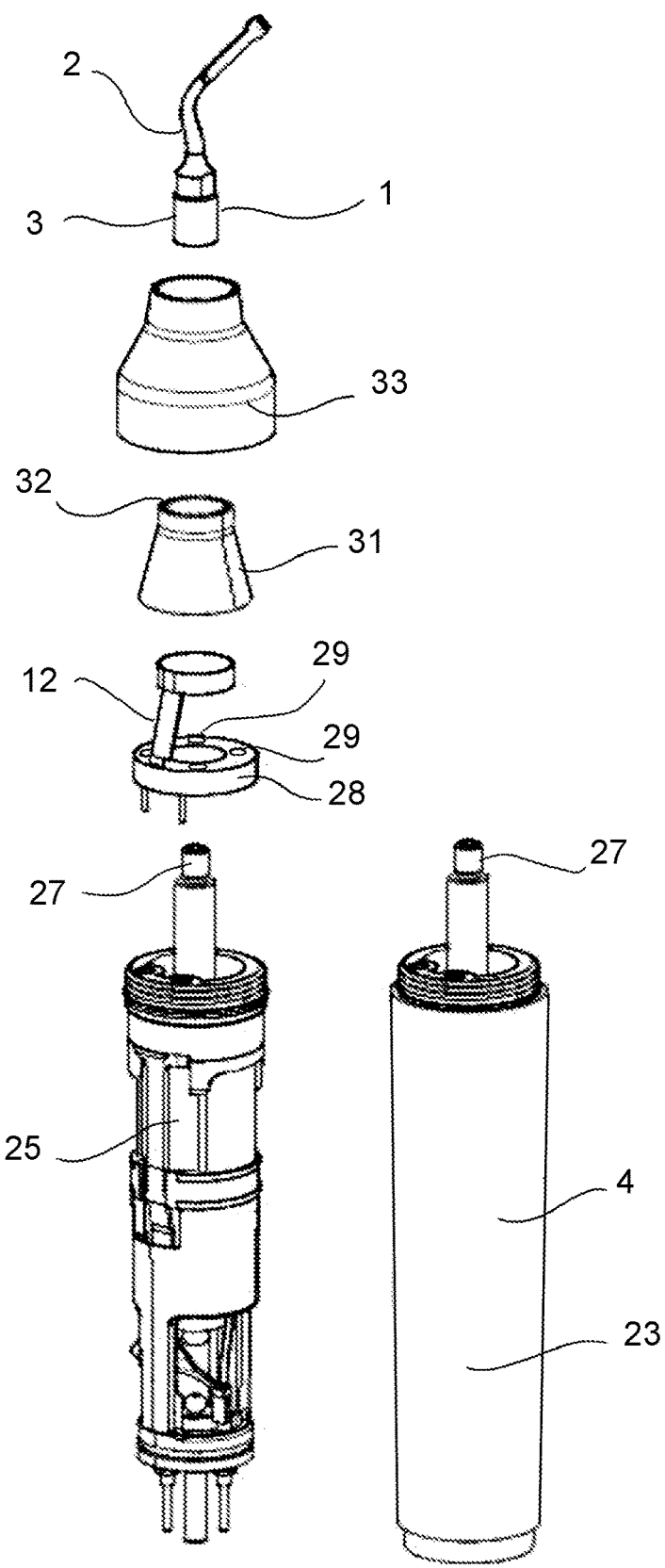
FIG. 3 shows an axonometric view with parts separated of some components of the handpiece assembly and insert assembly of FIG. 1 in which the insert assembly, the handpiece distal portion lid, the light guide with light concentrators, the handpiece antenna supported by the handpiece antenna connection element and the inner handpiece components, such as the piezoelectric transducer, are shown.
FIG. 4 depicts an axonometric view of only the central portion of the handpiece without the distal portion lid and the handpiece antenna highlighting the transducer shaft insert connection tang for the solid interchangeable connection of insert assemblies.
Figure 5:
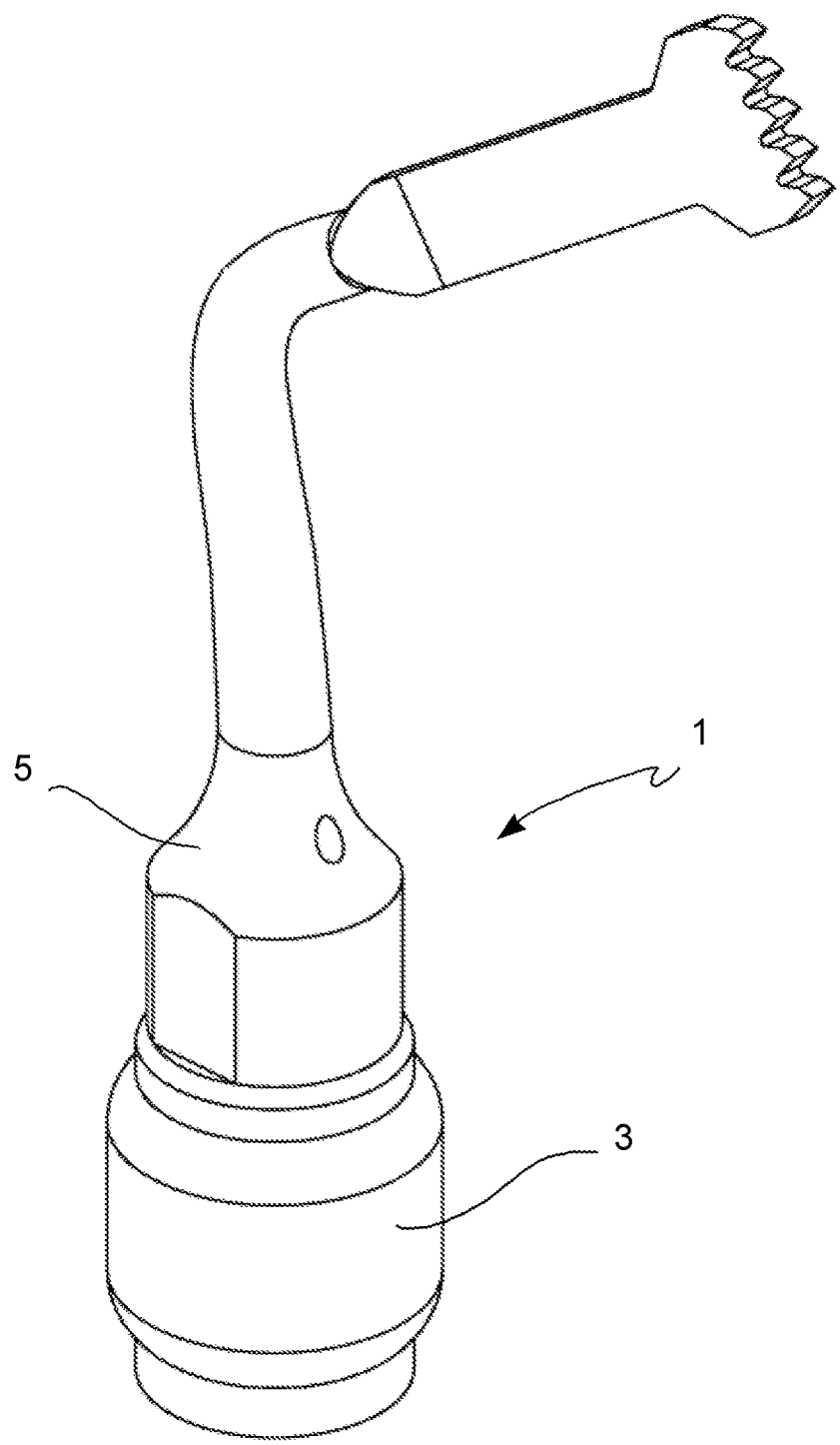
FIG. 5 depicts an axonometric view of an insert assembly.
Figure 6:
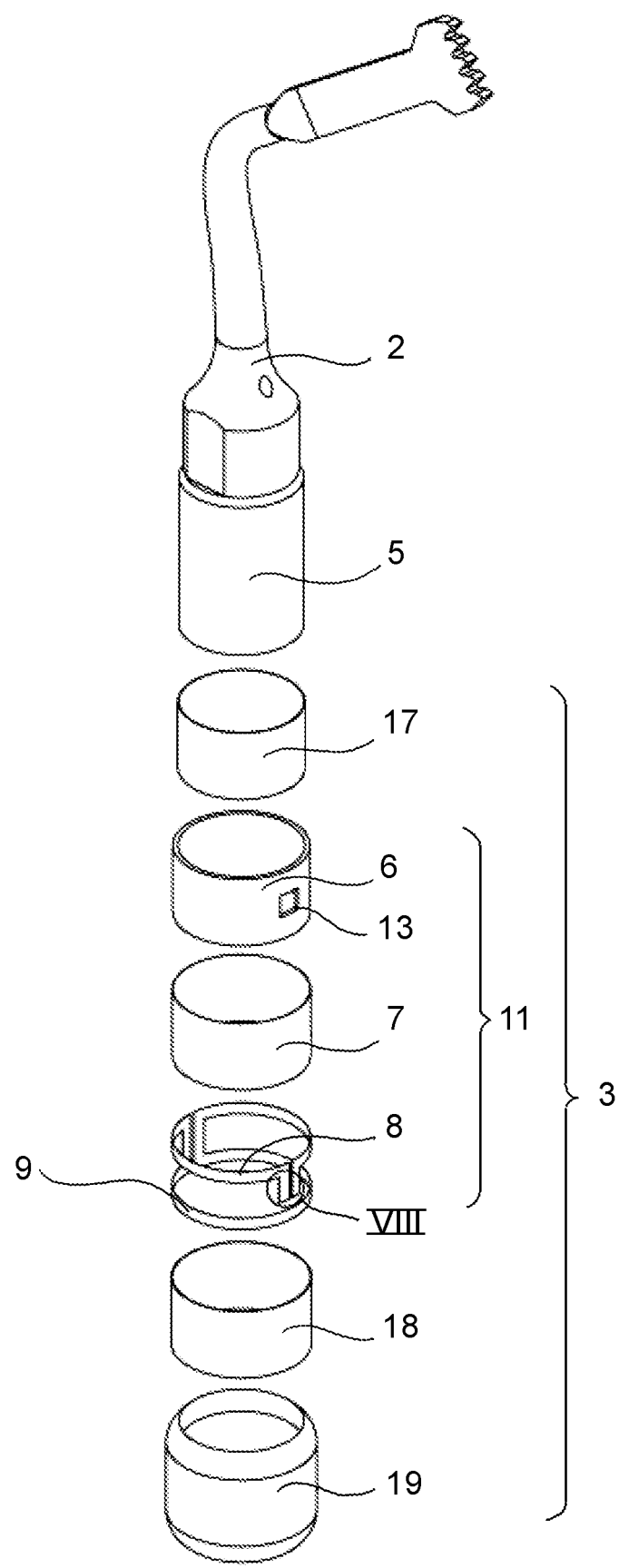
FIG. 6 shows an axonometric view with parts separated of the insert of FIG. 5 in which the different layers of a radiofrequency identifier are highlighted.
Figure 7:
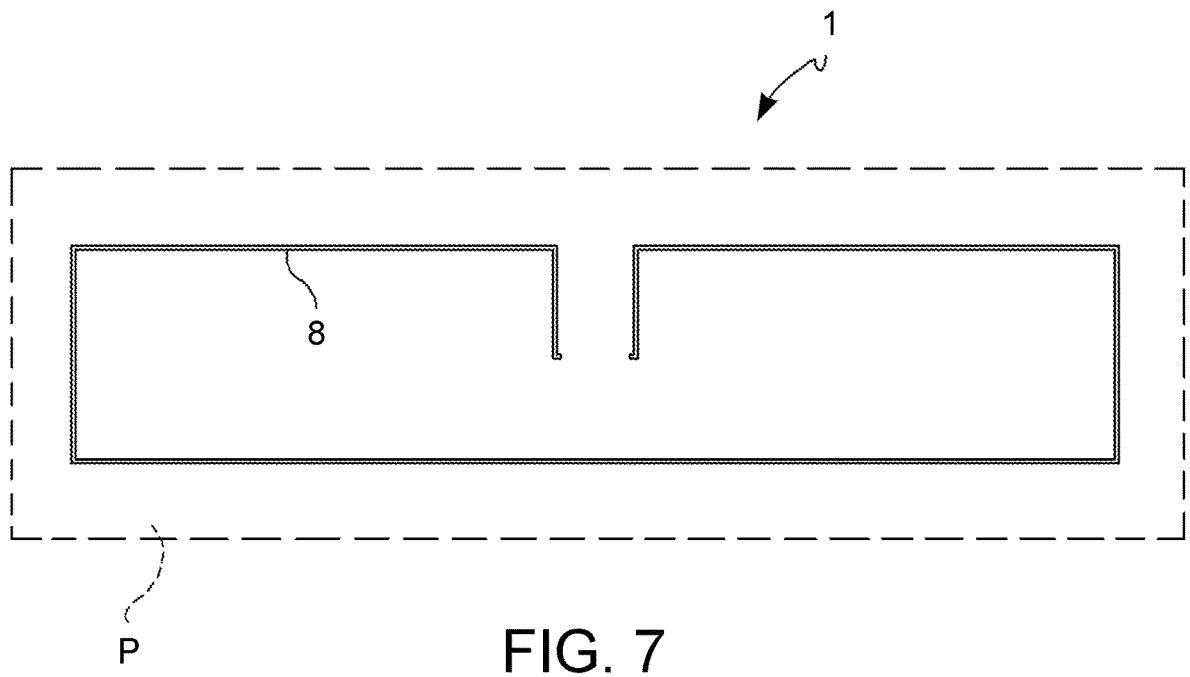
FIG. 7 shows an enlarged plan view of the insert antenna in the extension of the planar profile thereof adapted to wrap and surround or partially surround the insert foot of an insert.
Figure 8:
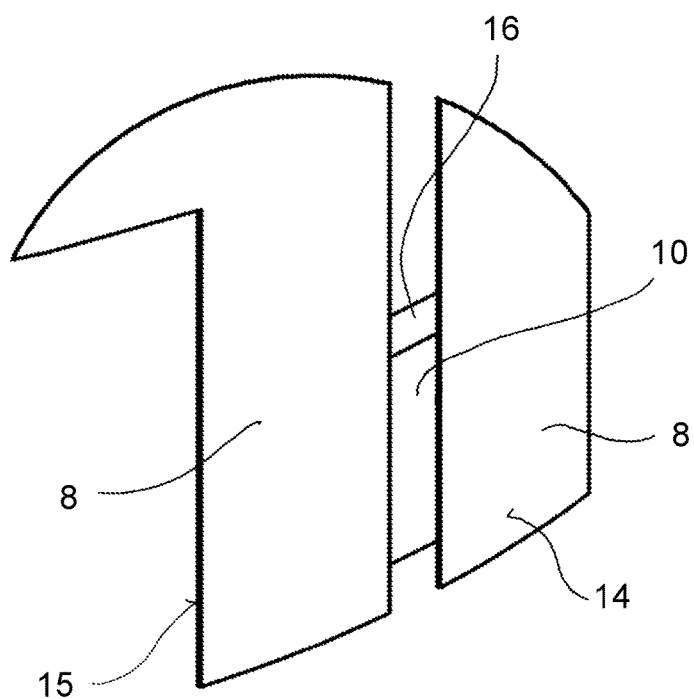
FIG. 8 depicts an axonometric view of a detail (indicated as VIII in FIGS. 6 and 17) of an insert antenna to which an identification chip is connected, so as to arrange said identification chip with the entire body thereof protruding from only one side of the extension plane of said insert antenna.
Figure 9:
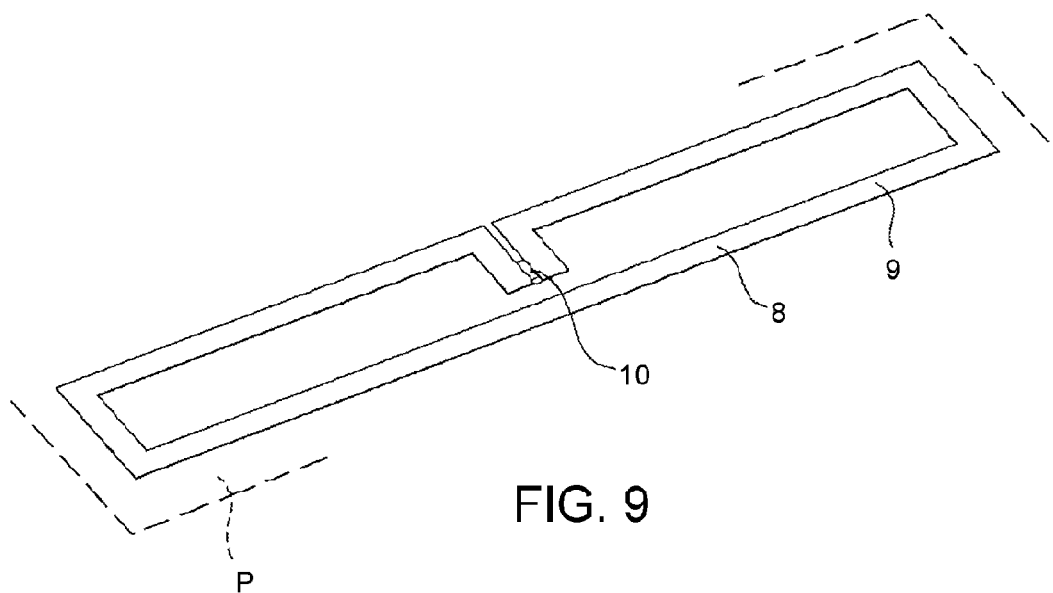
FIG. 9 depicts an axonometric view of a further embodiment of an insert antenna connected to an identification chip.
Figure 10:
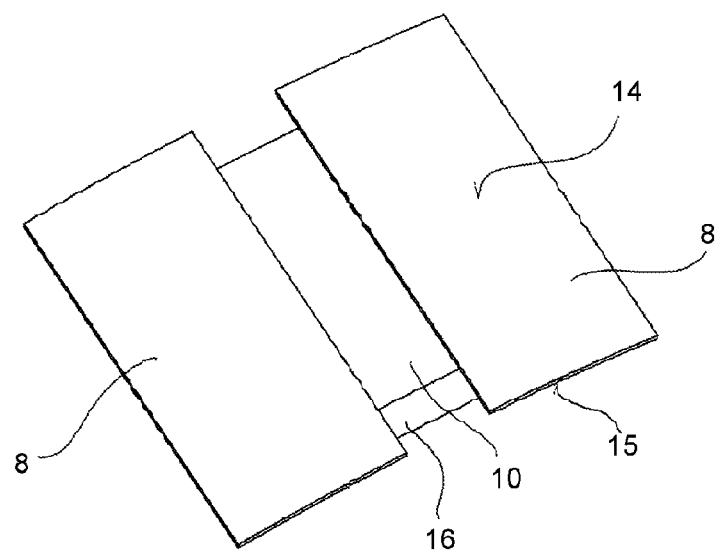
FIG. 10 depicts an axonometric view of a detail of the insert antenna of FIG. 9 in the detail where the identification chip is connected, so as to arrange said identification chip protruding with the entire body thereof from only one side of the extension plane of said insert antenna.
Figure 11:
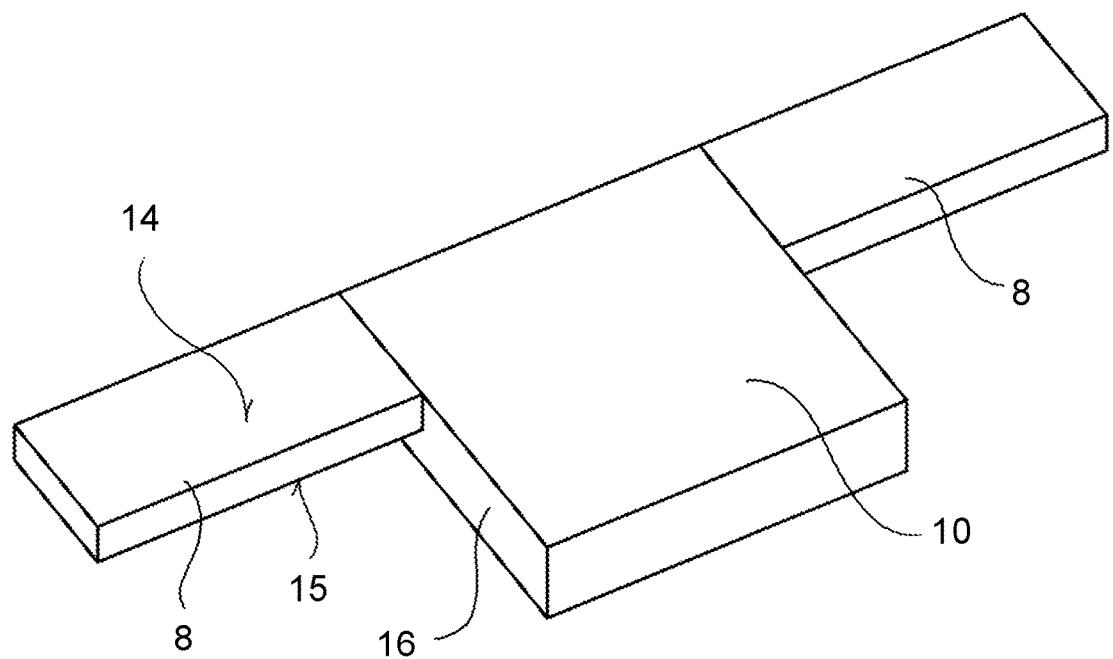
FIG. 11 depicts an axonometric view of a detail of an insert antenna to which an identification chip is connected, so as to arrange said identification chip with the entire body thereof on the same body level as said insert antenna and partially beyond or protruding beyond only one side of the extension plane of said insert antenna.
Figure 12:
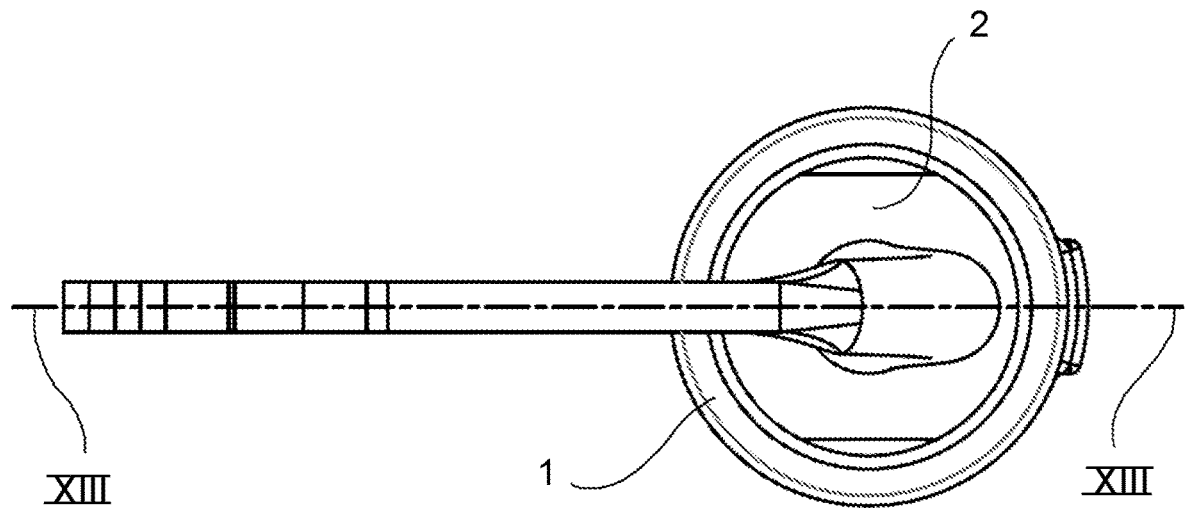
FIG. 12 shows a top view of an insert assembly.
Figure 13:
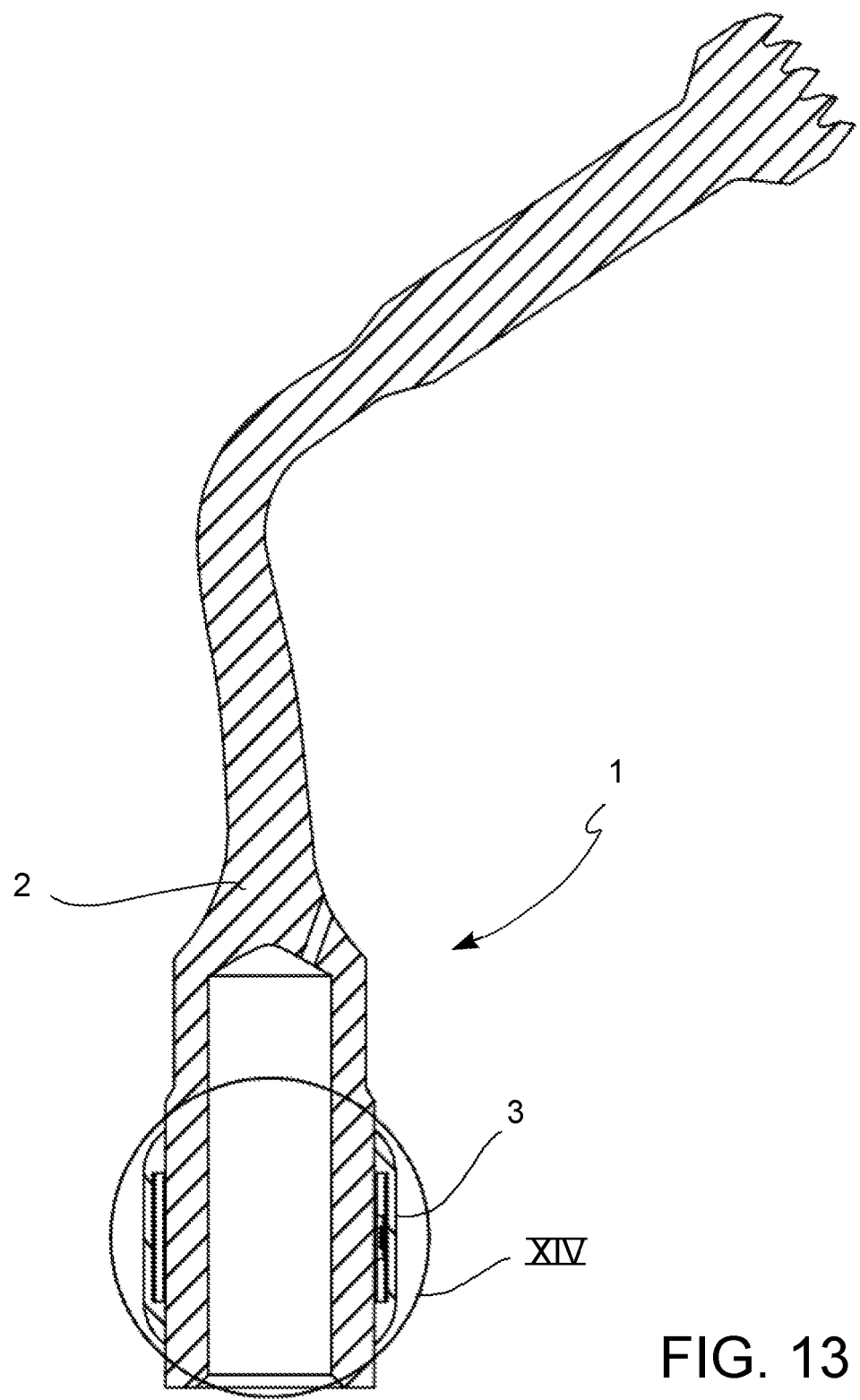
FIG. 13 shows a section taken along line XIII-XIII of FIG. 12 of the insert of FIG. 12 in which the radiofrequency identifier is highlighted.
Figure 14:
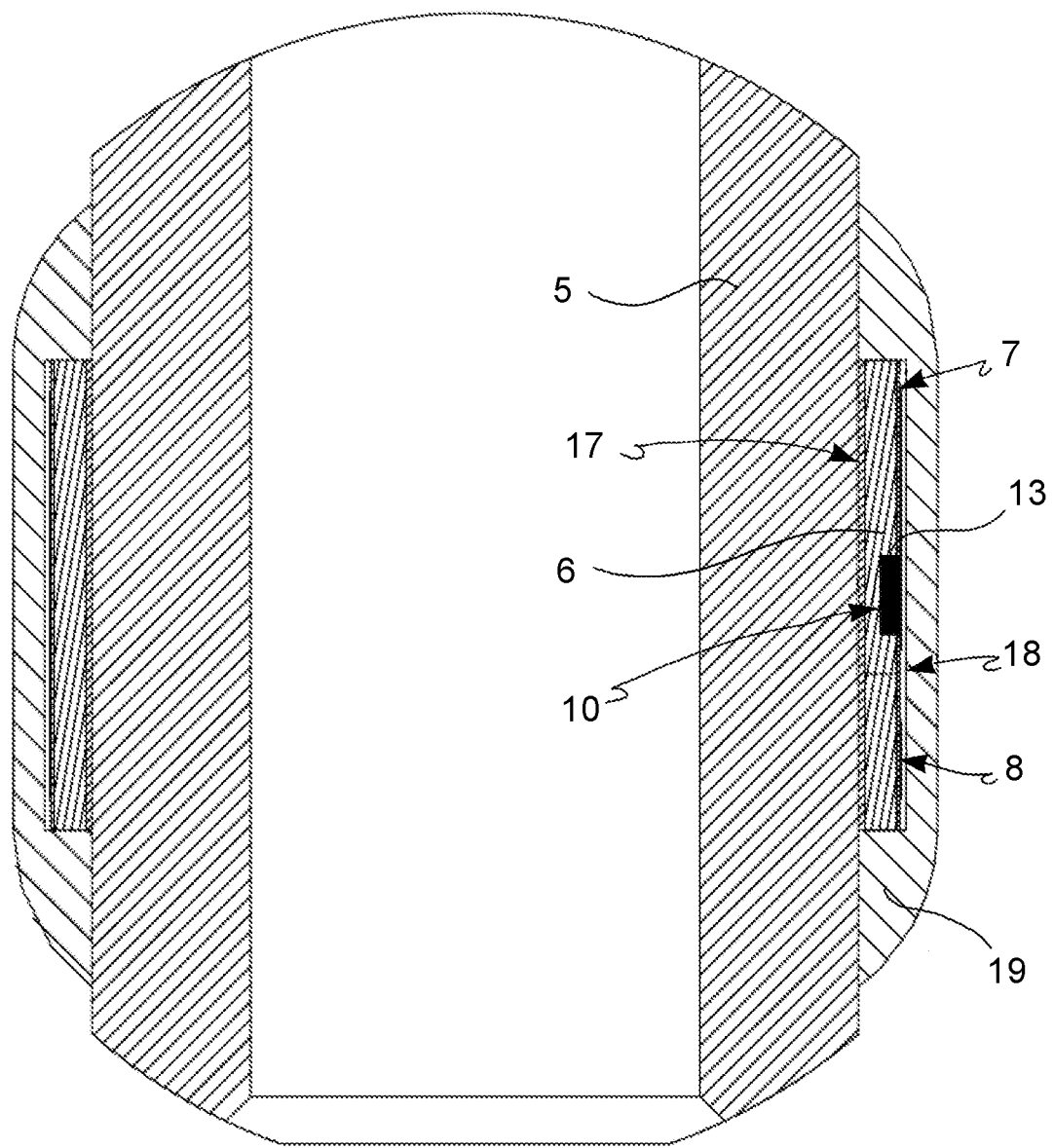
FIG. 14 shows the enlargement indicated with XIV of FIG. 13 in which the layers of the radiofrequency identifier are highlighted.
Figure 15:
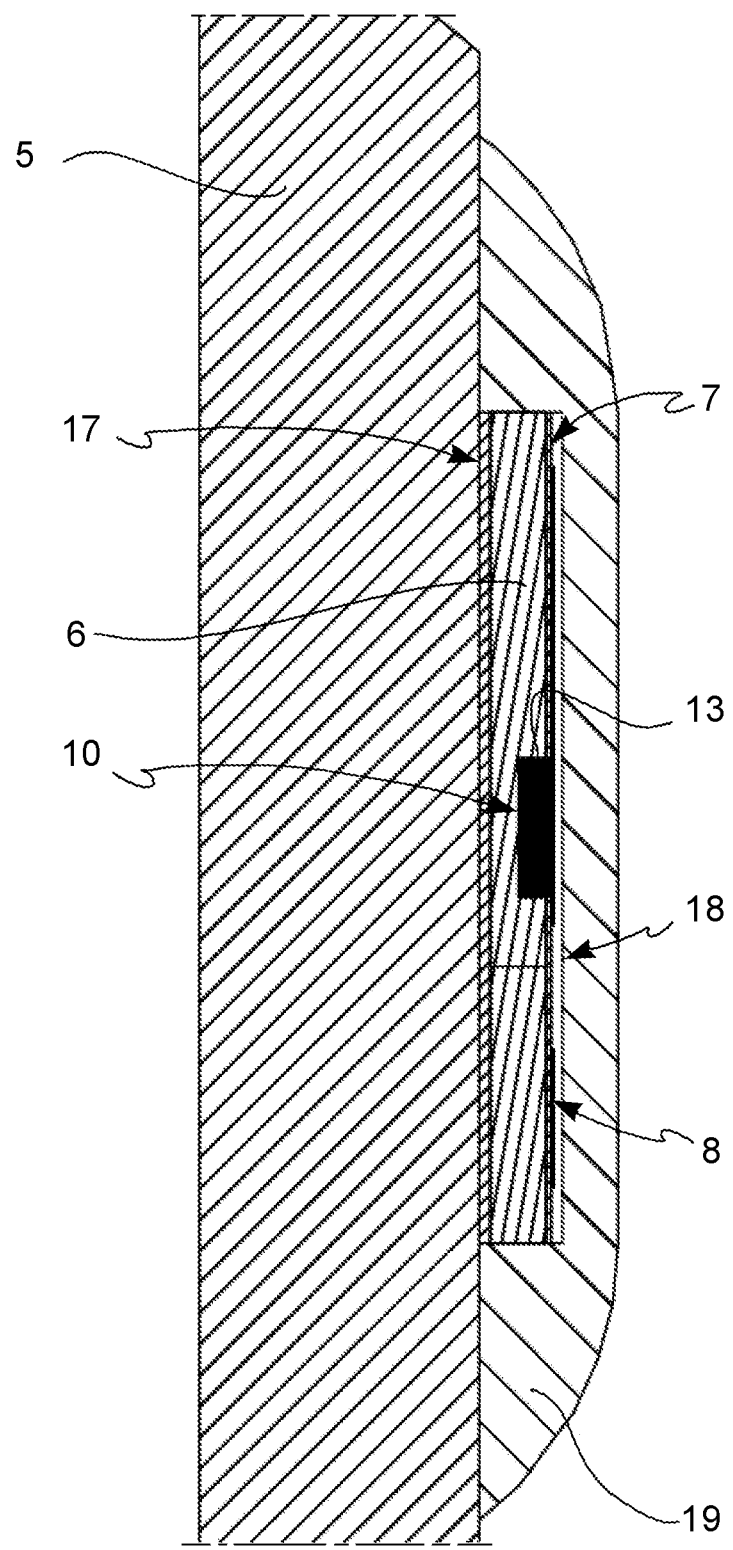
FIG. 15 shows a section view of the enlargement of FIG. 14.
Figure 16:
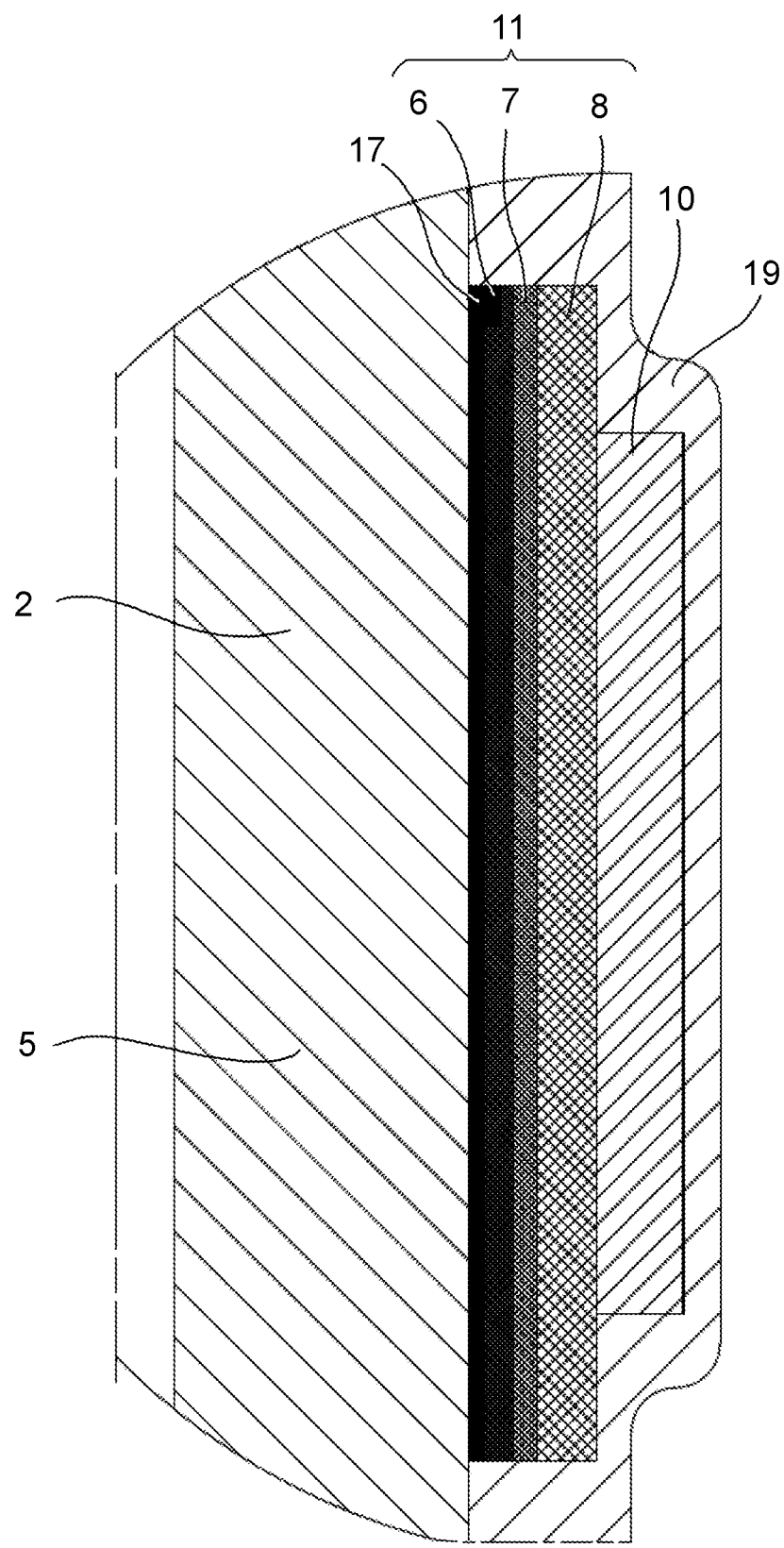
FIG. 16 depicts a detail of a cross-section of an insert assembly according to a further embodiment.
Figure 17:
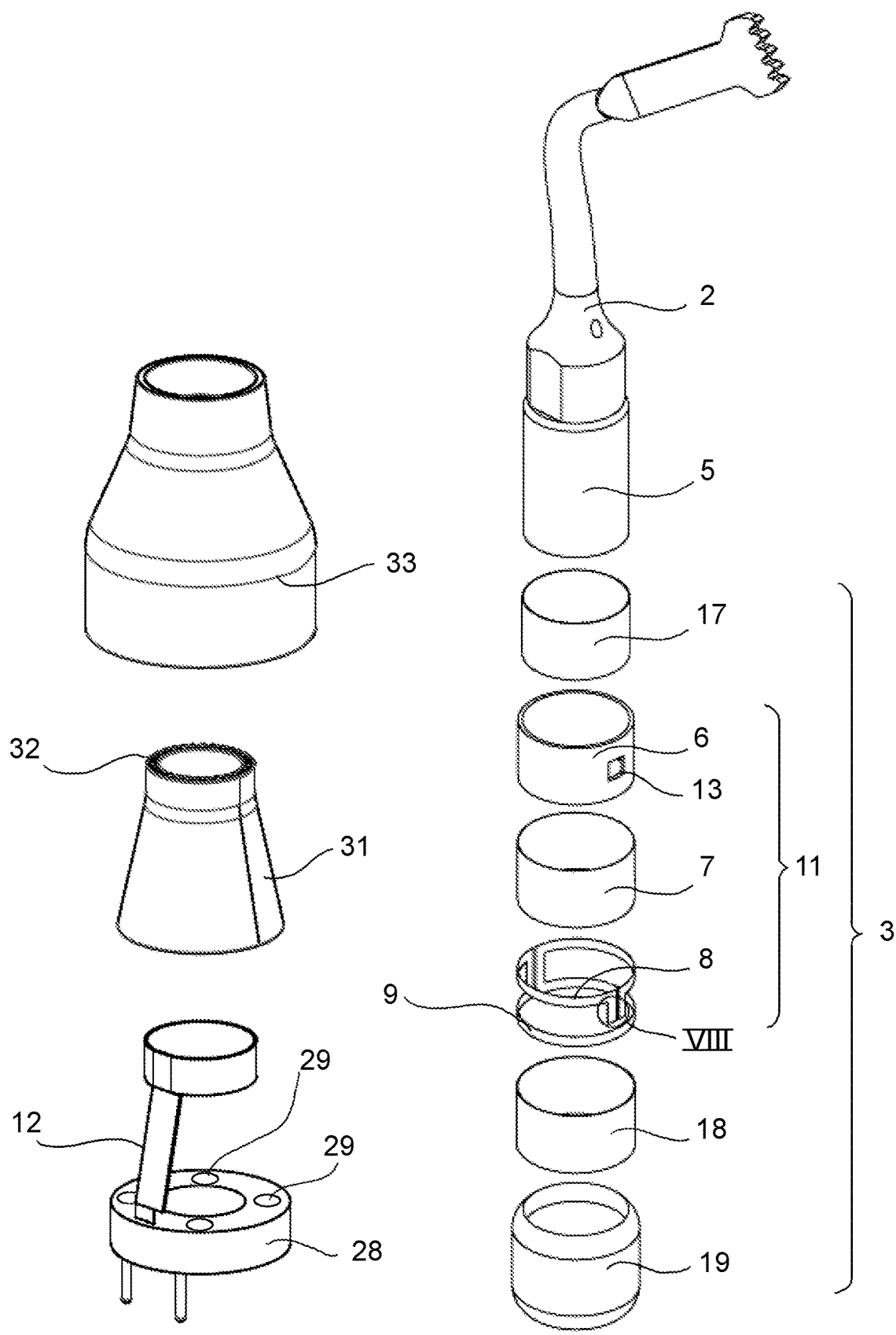
FIG. 17 depicts an axonometric view with parts separated of a handpiece antenna together with the components of the handpiece distal portion and an insert assembly comprising the various layers of a radiofrequency identifier associated with an insert.

In FIG. 1, reference numeral 101 identifies an ultrasonic system 101 as a whole comprising generator means 102 or control element 21 operatively connected to a transducer 25 which generates ultrasonic micro-vibrations, which generate vibrations in a connected insert 2.

By way of example only, an ultrasonic system 101 is a surgical or prophylactic device, e.g., a dental or medical device. According to other embodiments, the present ultrasonic system 101 is an industrial instrument.

An insert assembly 1 with radiofrequency identifier 3 is described hereinafter. Such an insert assembly 1 is adapted to be inserted into a handpiece 4 of a medical device.

The insert assembly 1 comprises, according to a general embodiment thereof, an insert 2, a ferromagnetic layer 6, a dielectric layer 7, an insert antenna 8, and an identification chip 10.

The insert 2 is adapted to interact with a part of the patient's body and comprises at least one insert metal tang 5.

The ferromagnetic layer 6 is arranged in contact with, or on the part of, the aforementioned insert metal tang 5 of the insert 2.

In accordance with an embodiment, said ferromagnetic layer 6 is glued to said insert metal tang 5 of the insert 2. In accordance with a different embodiment, said ferromagnetic layer 6 is applied to said metal tang 5 by interposing a double-sided adhesive.

The ferromagnetic layer 6 comprises ferromagnetic material.

The dielectric layer 7 is arranged in contact with the aforesaid ferromagnetic layer 6.

The insert antenna 8 is arranged in contact with the aforesaid dielectric layer 7 and comprises a metal insert antenna element 9, which extends along a predefined, essentially planar profile P. Said profile P, as a whole, wraps, at least partially surrounding said metal tang 5.

Such an insert antenna 8 is configured to receive and transmit electromagnetic fields, either modulated or non-modulated, within a given frequency range.

An identification chip 10 is operatively connected to the aforesaid insert antenna 8 and is configured to transmit, when activated, information related to the insert assembly 1.

The aforesaid ferromagnetic layer 6 is adapted to reduce or cancel phenomena of attenuation and/or distortion of the electromagnetic field caused by field parasitic effects in the vicinity of the insert antenna 8 due to the interaction of a transmitted/received electromagnetic field with metal parts of the insert metal tang 5 of the insert 2 and/or with liquids present in the insert 2 and/or with the metal insert antenna element 9.

The aforesaid ferromagnetic layer 6, dielectric layer 7, and insert antenna 8 form a transceiver device 11, adapted to put the identification chip 10 in wireless communication with a handpiece antenna 12 included in the handpiece 4 into which the insert assembly 1 is adapted to be inserted.

According to a further embodiment, an insert assembly 1 comprises an insert 2 and a radiofrequency identifier 3.

Said insert assembly 1 is adapted to be inserted into a medical device handpiece 4.

Said insert assembly 1 comprises:
the insert 2 adapted to interact with a part of the patient's body, in which the insert 2 comprises an insert metal tang 5;
the radiofrequency identifier 3.

Said radiofrequency identifier comprises a ferromagnetic layer 6, arranged on the side of said insert metal tang 5 of the insert 2, in other words directly in contact considering a layer of glue or double-sided adhesive interposed between said ferromagnetic layer 6 and said insert metal tang 5.

Said ferromagnetic layer 6 comprises ferromagnetic material. In particular, said ferromagnetic layer 6 is adapted to reduce or cancel phenomena of attenuation and/or distortion of the electromagnetic field caused by field parasitic effects in the vicinity of an insert antenna 8 due to the interaction of a transmitted/received electromagnetic field with metal parts of the metal insert tang 5; and/or with liquids present in the insert and/or with the metal insert antenna element 9.

Said radiofrequency identifier further comprises a dielectric layer 7, arranged in contact with said ferromagnetic layer 6.

Said radiofrequency identifier further comprises said insert antenna 8, arranged in contact with said dielectric layer 7, and comprises an insert antenna metal element 9, which extends along a predefined, essentially planar profile P. Said profile P, as a whole, wraps, at least partially surrounding said metal tang 5. For example, said profile P lies on a cylindrical surface.

Said insert antenna 8 is configured to receive and transmit electromagnetic fields within a given frequency range, either modulated or non-modulated.

Said radiofrequency identifier further comprises an identification chip 10.

Said identification chip 10 is operatively connected to said insert antenna 8, and is configured to transmit, when activated, information related to the insert assembly 1.

Additionally, said medical device handpiece 4 comprises a handpiece antenna 12.

Said ferromagnetic layer 6, dielectric layer 7, and insert antenna 8 form a transceiver device 11, adapted to put said identification chip 10 in wireless communication with said handpiece antenna 12 of said handpiece 4.

In accordance with an embodiment of the insert assembly 1, the aforesaid dielectric layer 7 is distinct from the aforesaid ferromagnetic layer 6. Furthermore, the dielectric layer 7 is interposed between the ferromagnetic layer 6 and the insert antenna 8, so as to electrically isolate the aforesaid metal insert antenna element 9 of the insert antenna with respect to the ferromagnetic material of the ferromagnetic layer 6.

Advantageously, said ferromagnetic layer 6 and/or said dielectric layer 7 comprises a chip seat 13.

Said identification chip 10 is operatively connected to said insert antenna 8 in such a way to avoid protruding from at least a first side, or outer side 14, of said substantially flat profile P of said metal insert antenna element 9 of said insert antenna 8.

Furthermore, said identification chip 10 protrudes with a chip portion 16 thereof from the opposite side, with respect to said outer side 14 of said substantially planar profile P, protruding from the inner side 15 of said metal insert antenna element 9 of said insert antenna 8.

Advantageously, said protruding chip portion 16 is received in said chip seat 13, making said radiofrequency identifier particularly compact and space-saving.

Furthermore, the insertion of said protruding chip portion 16 into said chip seat 13 further shields said identification chip 10 making it more robust to external electromagnetic disturbances and also the assembly of said identification chip 10 and said insert antenna 8 more mechanically robust to external stresses and more thermally protected from thermal stresses, e.g., applied by sterilization autoclaves or instrument cleaners.

In accordance with an embodiment, said ferromagnetic layer 6, said dielectric layer 7 and said insert antenna 8 form a stack of dimensions in the range between 50 micrometers and 800 micrometers, preferably between 100 micrometers and 600 micrometers and adapted to be placed above an insert with dimensions transverse to the longitudinal extension thereof, e.g., radial dimensions at one of the longitudinal extension axes thereof, not exceeding 6,400 micrometers. These values refer to the thickness of the stack on the plane, thus they correspond to the increase of the radius of the insert 2 where, by way of example, it is cylindrical, while the radial dimensions of the insert are the diameter of the metal of insert 2 where, for example, it is cylindrical.

In accordance with an embodiment, the thickness of the ferromagnetic layer 6, i.e. the radial dimension relative to the longitudinal extension of the insert 2 is in the range between 20 micrometers and 400 micrometers, preferably between 50 micrometers and 300 micro-meters.

In accordance with an embodiment, an inner insulating layer 17, e.g., double-sided adhesive, is arranged internally with respect to said ferromagnetic layer 6, i.e., between said insert metal tang 5 and said ferromagnetic layer 6.

In accordance with an embodiment, said dielectric layer 7 is made of double-sided adhesive.

In accordance with an embodiment, said insert antenna 8 is made of aluminum.

In accordance with an embodiment, said insert antenna 8 has a flat rectangular shape and dimension of the rectangle sides respectively of the short side between 1 mm and 6 mm, preferably between 2 mm and 4 mm, and of the long side between 10 mm and 30 mm and preferably between 12 mm and 25 mm, and thickness of said insert antenna 8 less than 50 micrometers.

In accordance with an embodiment, said radiofrequency identifier 3 further comprises an outer insulating layer 18, arranged externally with respect to said ferromagnetic layer 6, dielectric layer 7, identification chip 10 and insert antenna 8.

In accordance with an embodiment, said radiofrequency identifier 3 further comprises a protective layer 19, e.g., biocompatible, arranged externally with respect to said ferromagnetic layer 6, dielectric layer 7, identification chip 10 and insert antenna 8.

In accordance with an embodiment, said radiofrequency identifier 3 further comprises a protective layer 19, e.g., biocompatible, arranged externally with respect to said outer insulating layer 18.

In accordance with an embodiment, said outer insulating layer 18 is made of PVC (polyvinyl chloride), or PET polyethylene terephthalate, or polyamide, e.g., Kapton®.

In accordance with an embodiment, said protective layer 19 is biocompatible, e.g., a paint or an epoxy compound with one or more components.

In accordance with an embodiment, said ferromagnetic layer 6, said dielectric layer 7 and said insert antenna 8 form a stack.

In accordance with an embodiment, said ferromagnetic layer 6, said dielectric layer 7 and said insert antenna 8 wrap said insert metal tang 5 forming a substantially concentric structure about said central metal element 5. The term "concentric" does not mean that the structure is totally circling the central metal element nor that it must be perfectly concentric thereto, but only that it embraces the inner metal element along a portion of the periphery of the central metal element, e.g., to allow a minimum extension of said insert antenna about the periphery of the insert, an extension adapted to the desired transceiver.

In accordance with an embodiment, such a ferromagnetic layer 6 comprises ferrite. In accordance with an embodiment, said ferromagnetic layer 6 is made of thin sintered ferrite with high permeability or a polymer base, mixed with magnetic powders of micrometric size dispersed throughout the material.

In accordance with an embodiment, said ferromagnetic layer 6 said identification chip 10 is an RFID TAG chip.

In accordance with an embodiment, said identification chip 10 has a parallelepiped-shape with base side dimensions between 50 micrometers and 1200 micrometers, preferably between 100 micrometers and 1000 micrometers, and thickness less than 300 micrometers.

In accordance with an embodiment, said insert assembly 1 is configured to operate in association with a medical device for dental or prophylactic or implantology and medical applications in the maxillofacial or craniofacial or neuro-spinal or orthopedic or other anatomical districts.

The present invention further relates to a medical device 20 comprising a control element 21, a medical device handpiece 4 provided with a handpiece antenna 12 for RF transceiver and an insert assembly 1 according to any one of the embodiments described above.

In accordance with an embodiment, said insert assembly 1 is operatively and mechanically connected separably from said handpiece 4.

In accordance with an embodiment, said medical device handpiece 4 comprises a handpiece distal portion 22 which ends with a distal handpiece end 30, a handpiece central portion 23, and a handpiece proximal portion 24. A transducer 25, e.g., a piezoelectric transducer, is connected to an ultrasound generator or control unit 26. Said transducer 25 is received in said medical device handpiece 4 and an insert attachment tang 27 protrudes through said handpiece distal portion 22 removably connecting to said insert 2 so as to, when activated, put said insert 2 into resonance.

In accordance with an embodiment, said handpiece distal portion 22 comprises said handpiece antenna 12. In accordance with an embodiment, said handpiece antenna 12 removably connects to said handpiece 4. In accordance with an embodiment, said handpiece antenna 12 is contained in said handpiece 4 and connects to said handpiece 4 in a fixed manner.

In accordance with an embodiment, said handpiece distal portion 22 comprises a handpiece antenna connection element 28.

Said handpiece antenna 12 is supported and electrically connected to said handpiece antenna connection element 28 and protrudes from said handpiece antenna connection element 28 towards said distal handpiece end 30 to at least partially overlap said insert antenna 8 when said insert is connected to said handpiece 4.

In accordance with an embodiment, said handpiece antenna 12 protrudes from said handpiece antenna connection element 28 towards said distal handpiece end 30 so as not to overlap said insert antenna 8 when said insert is connected to said handpiece 4.

In accordance with an embodiment, said handpiece antenna connection element 28 is electrically connected to said handpiece in a fixed or removable manner. Said handpiece antenna connection element 28 may comprise at least one LED 29.

In accordance with an embodiment, said handpiece antenna connection element 28 does not comprise LEDs 29.

In accordance with an embodiment, if said handpiece antenna connection element 28 comprises at least one LED 29, it may comprise a light guide element 31 comprising at least one light concentrator 32 associated with said handpiece antenna connection element 28 to guide the light of at least one LED 29 at the distal handpiece end 30 to illuminate the working area of said medical device 20.

In accordance with an embodiment, said light guide element 31, said handpiece antenna connection element 28 and said handpiece antenna 12 are covered by a handpiece distal portion lid 33, e.g., made of aluminum, removable connected to said handpiece distal portion 22.

In accordance with an embodiment, said medical device 20 connects said handpiece 4 to said ultrasound generator or control unit 21 by means of a connection cable 34 for electrical and fluidic supply.

In accordance with an embodiment, said medical device handpiece 4 receives inserts 2 mechanically coupled to a device generating ultrasonic micro-vibrations, e.g., piezoelectric transducer 25, interchangeably, and operating at different frequencies and ranges of power and ultrasonic wave amplitude as a function of the chosen type of insert 2.

In accordance with an embodiment of the insert assembly, the insert antenna 8 is an RF antenna adapted to work at radiofrequency, the identification chip 10 is a radiofrequency identification chip and the aforesaid frequency range comprises one or more radiofrequency ranges.

In accordance with an embodiment of the insert assembly 1, the aforesaid transceiver device (hereinafter also referred to as a "transceiver structure") formed by ferromagnetic layer 6, dielectric layer 7 and insert antenna 8 can be modeled by means of an electrical circuit the electrical parameters of which depend on the size and material of the ferromagnetic layer 6.

According to an implementation option, the aforesaid transceiver structure formed by ferromagnetic layer 6, dielectric layer 7, insert antenna 8, and the identification chip 10, can be modeled by means of an LC electric circuit, in which the inductance La and capacitance Cc parameters depend on the dimensions and material of the ferromagnetic layer 6, dielectric layer 7, insert antenna 8 and identification chip 10. In particular, the inductance La depends mainly on the dimensions and material of the ferromagnetic layer, the dielectric layer, and the insert antenna, while the capacitance Cc depends mainly on the identification chip 10.

In this case, the frequency range over which the transceiver structure is able to operate depends on the aforesaid inductance La and capacitance Cc parameters. In fact, in the absence of other elements in the LC circuit, the resonance frequency is obtained from the well-known formula $f_0 = 1/[2\pi(L_a C_c)^{1/2}]$.

It should be noted that the ferromagnetic layer contributes to the inductance value La, by electromagnetic coupling, but if it is electrically isolated from the metal part of the insert antenna, it does not introduce a further element into the equivalent electrical circuit. Instead, if the ferromagnetic material were in contact, even only partially, with the metal part of the insert antenna, it would introduce a further equivalent element into the electrical circuit model, corresponding to a non-linear impedance depending on the voltage, thus causing an undesired and uncontrollable perturbation of the resonance frequency.

In this regard, the previously mentioned embodiment is particularly advantageous, in which the dielectric layer 7 is interposed between the ferromagnetic layer 6 and the insert antenna 8, so as to electrically isolate the metal insert antenna element 9 of the insert antenna with respect to the ferromagnetic material of the ferromagnetic layer 6. In fact, due to this feature, the problems caused by a contact (either imperfect or complete isolation) between the ferromagnetic material and the metal parts of the antenna are eliminated, problems which would compromise the stability, repeatability and efficiency properties of the transceiver system, and could not ensure a single and stable resonance frequency on the design value.

In fact, the dielectric layer, arranged in such a way to separate the antenna from the ferromagnetic layer, performs the function of isolating the resonant RFID system from external perturbations, ensuring the stability and reproducibility thereof also and above all at the high frequencies (mentioned below) at which, advantageously, the resonant RFID system of the insert assembly of the present invention is adapted to operate.

According to an option of use of the insert assembly, the operating frequency ranges of the transceiver structure comprise frequency ranges in the UHF RFID band (between 860 MHz and 960 MHz): for example, 865-868 MHz ETSI European technical standard, 902-928 MHz FCC FHSS North American technical standard, 916.7-920.9 MHz and 916.7-923.5 MHz MIC LBT Japanese technical standard, 902-907.5 MHz, and 915-928 MHz ANATEL FHSS Brazilian technical standard, 920.5-924.5 MHz MII FHSS Chinese technical standard.

According to an implementation option of the insert assembly, the thickness of the ferromagnetic layer, i.e., the radial dimension with respect to the insert is in the range between 20 micrometers and 400 micrometers.

More preferably, the thickness of the ferromagnetic layer, i.e., the radial dimension with respect to the insert, is in the range between 50 micrometers and 300 micrometers.

According to different possible implementation options of the insert assembly, the ferromagnetic layer is made of thin sintered ferrite with high permeability or a polymer base, mixed with magnetic powders of micrometric size dispersed throughout the material.

According to an embodiment of the insert assembly 1, the identification chip 10 is an RFID chip (e.g., an RFID chip known in itself).

In accordance with an embodiment of the insert assembly 1, the identification chip 10 is configured to store, and to transmit, when excited, through the aforesaid transceiver structure, one or more items of information belonging to the following set:

- unique and non-modifiable identification code information of the insert assembly;
- information related to the manufacturer and traceability of the insert assembly, and/or one or more types of medical instruments in which the insert assembly may operate;

information about the operating frequency ranges in which the transceiver structure of the insert assembly can operate;

information that the insert screwed to the handpiece is appropriate for the type of surgery selected in the medical device;

information about the history of modes and times of use;

information about the integrity of the insert assembly to maximize the efficiency and effectiveness of the clinical-surgical phase towards the patient;

information about the integrity of the insert assembly for appropriate scheduled maintenance;

information about whether or not the insert assembly is inserted correctly, if the insert assembly is inserted in a respective handpiece;

information about operating parameters of the insert tip assembly and/or error or alarm messages in the presence of anomalous operating situations.

According to an example of use, the insert assembly is configured to operate in association with a medical device for dental or prophylactic or implantology and medical applications in the maxillofacial or craniofacial or neurospinal or orthopedic or other anatomical districts.

A medical device according to the present invention is described here.

Such a medical device comprises a control unit, a handpiece with a handpiece antenna and an insert assembly according to any one of the embodiments described above, in which such an insert assembly is operatively and mechanically connected to the aforesaid handpiece of the medical device, and in which the insert antenna is configured to communicate wirelessly with the handpiece antenna.

Figure 18:
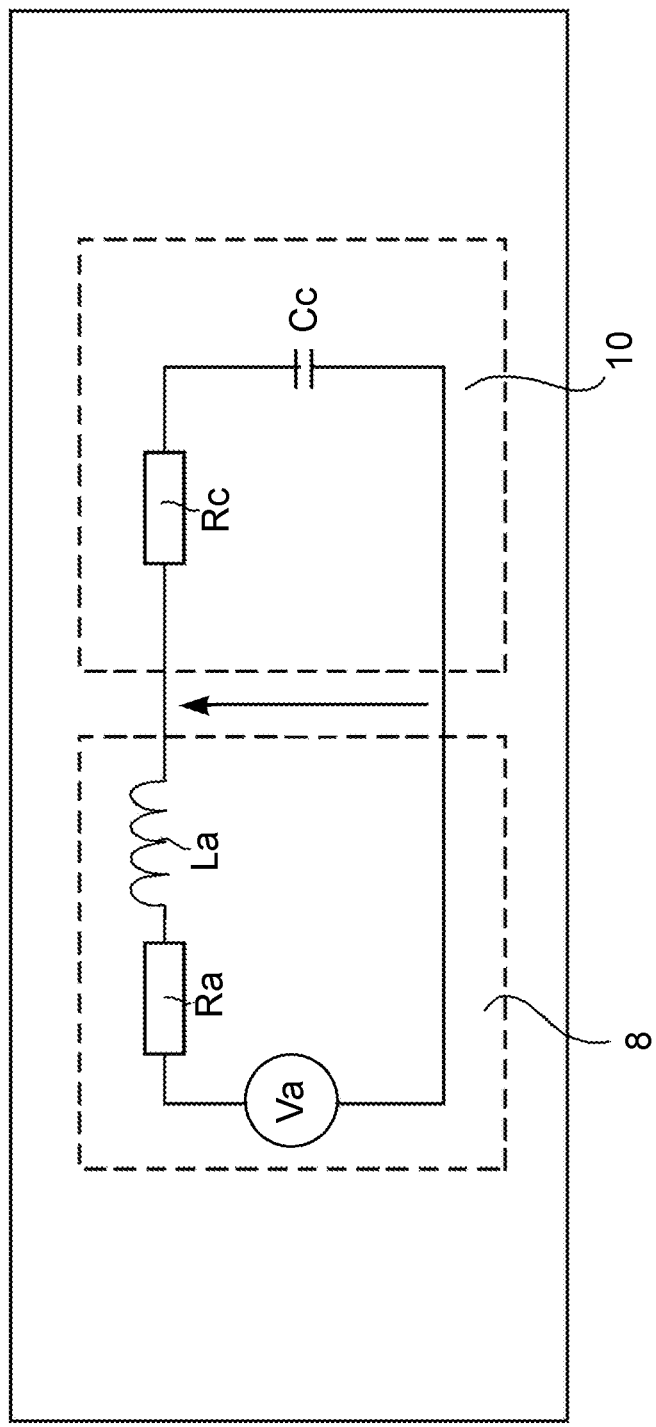
FIG. 18 shows an example of an equivalent electrical circuit, in a serial representation, of the assembly consisting of the RFID identification chip and the insert antenna.
Figure 19:
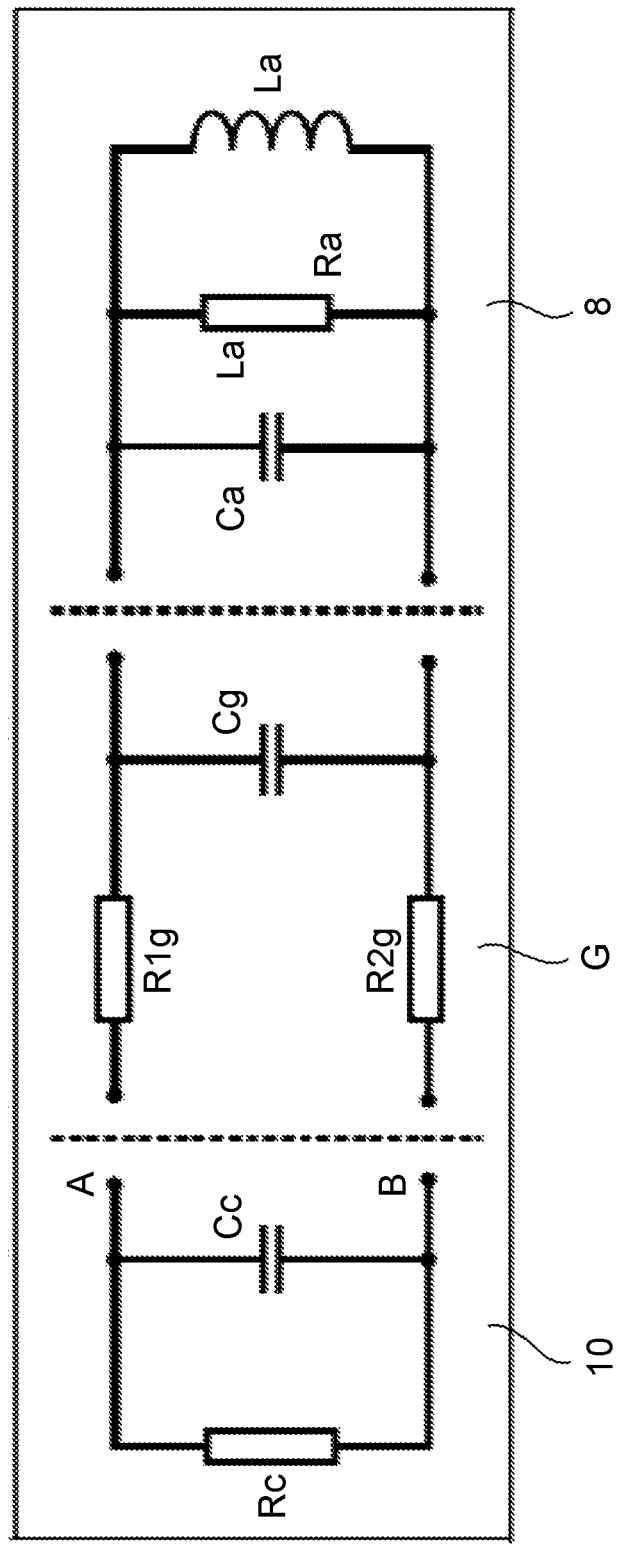
FIG. 19 shows a parallel representation of another example of an equivalent electrical circuit of the assembly consisting of the RFID identification chip and the insert antenna, also including a connection model.
Figure 20:
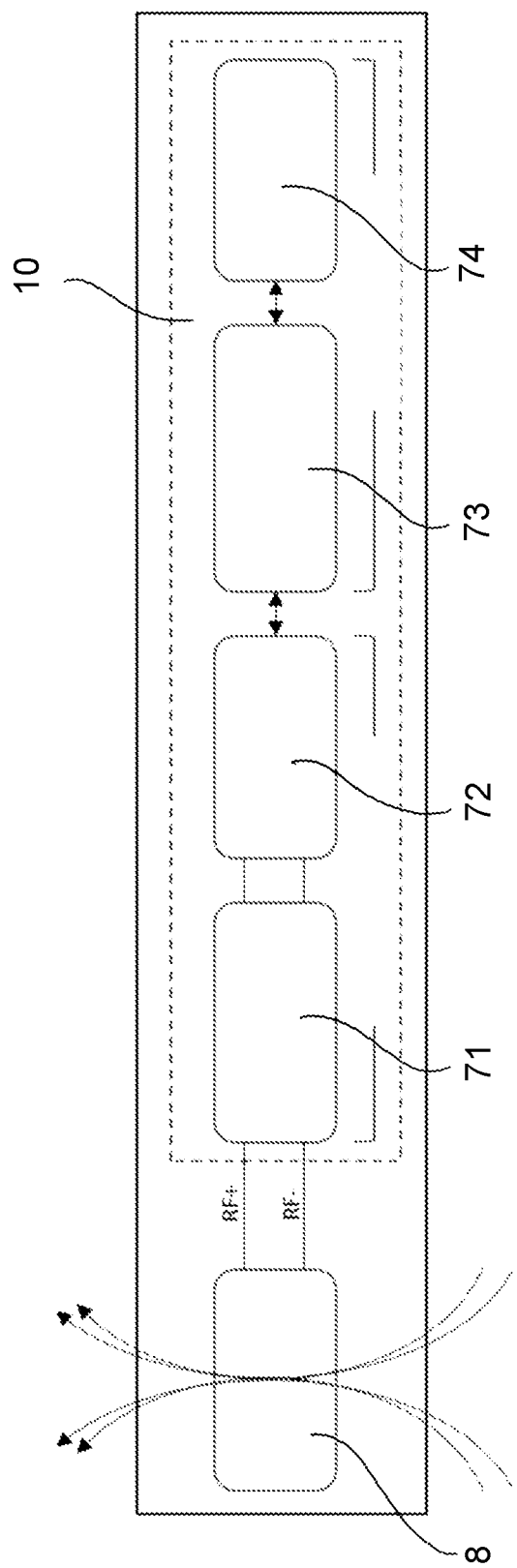
FIG. 20 depicts a block diagram of an embodiment of the insert antenna and the identification chip.

With reference to FIGS. 18-20, further information about possible embodiments of the insert assembly will be given hereinafter.

FIG. 18 shows an equivalent electrical circuit in a series representation of the assembly consisting of the RFID identification chip 10 and the insert antenna 8. Ignoring the parasitic capacitance of the whole, the identification chip 10 is modeled by a capacitance Cc and a resistor Rc; the insert antenna 8 is modeled by an inductance La and a resistor Ra. Indeed, the overall electrical circuit is an LC circuit, while the resistive components take "non-ideal situations" into account, i.e., radiated system losses and energy losses.

Such a model is an embodiment in which the wireless transceiver structure is based on Near Field UHF technique (860 MHz÷960 MHz), and exploits the reactive part of the electromagnetic field, which is operating as a so-called "magnetic antenna" with preferably segmented closed-loop geometry.

From the point of view of the fields, the ferromagnetic layer has the function of isolating the wireless transceiver structure from the metal parts of the insert body, thus preventing the creation of the reflected antagonist field caused by the stray currents induced by the variable primary magnetic field, thus avoiding the phenomena of attenuation or zeroing of the overall electromagnetic field.

In other words, the addition of the ferromagnetic layer, with a complex effective magnetic permeability, modifies the magnetic profile by influencing the mutual inductance and self-inductance. By appropriately selecting material and dimensions of the ferromagnetic layer (e.g., as in the above-mentioned implementation options) it is possible to have degrees of freedom to optimize the design of the transceiver structure, maximizing the intensity of the overall field present at the antenna, and improving communication as desired.

From a "concentrated parameters" electrical point of view, the ferromagnetic layer determines the effect of increasing the inductance of the LC system (where C is dominated by the chip). This feature, in turn, determines the additional effect of lowering the resonance frequency of the "antenna-chip" system, which has the advantage of bringing it within the limits required by the UHF band (and thus facilitating and improving the design of the transceiver structure, making it more easily adapted to the desired uses).

FIG. 19 shows a parallel representation of another example of an equivalent electrical circuit of the assembly consisting of the RFID identification chip 10 and the insert antenna 8, also including a model of the connection G. The depiction includes system parasitic elements, such as antenna parasitic capacitance.

In particular, in this case, the transceiver structure comprising the insert antenna 8 and the ferromagnetic layer 6 is modeled by means of an RLC circuit, while the identification chip 10 is modeled by means of an RC circuit.

From a substantial point of view, the considerations already made above in relation to FIG. 18 apply.

FIG. 20 depicts a block diagram of an embodiment of the insert antenna 8 and the identification chip 10.

In particular, the magnetic field lines are highlighted around the Near Field antenna 8.

In this embodiment, the identification chip 10 comprises an analog front-end (power management element 71 and modulator/demodulator element 72) and a digital control part, with a controller 73 (of a type known in itself, e.g. RFID tags) and a non-volatile memory 74.

As shown in paragraph 52 (ix-x-x-xi), the non-volatile memory 74 is configured to store use information, such as the cumulative sum of use time and statistically estimated degree of wear, so as to provide the clinician with an updated situation even if the inserts are used in places other than the original (clinician with several offices) but always with a suitable and compatible medical device.

According to a particular implementation option, to ensure data integrity and authenticity, the data can be stored in non-volatile memory 74 also after an encryption or password authentication process which can only be decoded by the appropriate medical device with which the insert can be associated.

A medical device handpiece assembly comprising a medical device handpiece 4 is described below. Such a handpiece 4 comprises a handpiece distal portion 22 adapted to receive by insertion an insert assembly 1 comprising a radiofrequency identifier 3, an insert antenna 8 and an insert 2 adapted to interact with a part of a patient's body (e.g., an insert assembly according to the embodiments described above).

The medical device handpiece assembly further comprises a handpiece antenna 12, arranged in the handpiece distal portion 22, and radiofrequency signal supply means, configured to provide the handpiece antenna 12 with a radiofrequency signal adapted to be transmitted by the handpiece antenna 12.

The aforesaid handpiece antenna 12 is configured to wirelessly communicate with the insert antenna 8 when said insert assembly is inserted into the handpiece 4 in an insertion region R included in the distal handpiece portion 22.

The aforesaid handpiece antenna 12 is a single-coil loop antenna, preferably a segmented ring antenna, comprising at least two handpiece antenna segments S1, S2, electrically arranged in series, which will be referred to as "first segment" S1 and "last segment" S2 hereinafter. A first end 41 of a first segment S1 of said at least two handpiece antenna segments is operatively connected to a first terminal 51 of said radiofrequency signal supply means, and a second end 42 of the aforesaid last segment S2 is operatively connected to a second terminal 52 of said radiofrequency signal supply means to form, around the aforesaid insertion region R, a coil radiating structure configured to generate in such an insertion region R an electromagnetic field with a radiofrequency dependent on the aforesaid radiofrequency signal.

The single-coil loop or each of the aforesaid at least two handpiece antenna segments (S1, S2) comprise a radiant metal element (S11, S21), characterized by a respective inductance L, electrically connected in series to a capacitive element (S12, S22), having a capacitance C such as to compensate, in the UHF RFID range (860 MHz÷960 Mhz), the effects due to the inductance L of the radiant metal element on currents circulating in the coil of the handpiece antenna 12.

According to an embodiment of the handpiece assembly, the aforesaid capacitance C of each of the capacitive elements (S12, S22) is such as to further adapt the characteristic impedance of the handpiece antenna 12 to a radiofrequency generator placed in a control element 21 of the medical device 20, operatively connected to the handpiece assembly.

According to an embodiment of the aforesaid handpiece, the aforesaid handpiece antenna 12 further comprises an input impedance adaptation first electrical network 43, included between the aforesaid first terminal 51 and second terminal 52 of the signal supply means and the aforesaid first end of first segment 41 and second end of last segment 42 of the handpiece antenna 12; and further comprising an antenna impedance adaptation second electrical network 44, included in the segmented antenna ring, and electrically connected in series between two segments (S1', S2') of the aforesaid at least two handpiece antenna segments.

According to an implementation option, the aforesaid input impedance adaptation first electrical network 43 comprises an LC inductance-capacitance circuit or a capacitive circuit.

According to an implementation option, the aforesaid antenna impedance adaptation second electrical network 44 comprises an RC resistance-capacitance circuit or a capacitive circuit, configured to adapt the antenna impedance to the desired impedance value, adapted to optimize the transmission of the radiofrequency signal generated by the medical device 21 and carried along the cable 34 and the handpiece 4.

For example, such an impedance value, in the UHF RFID range (860 MHz÷960 MHz) can be expressed with a complex number $Z=R+iX$ having a module between 20 ohms and 80 ohms, preferably between 45 and 55 ohms.

In accordance with an embodiment of the handpiece 4, the aforesaid radiant metal element (S11, S21) of the segmented ring antenna can be modeled by means of an equivalent electric circuit comprising an inductance L and a resistance R, in which said inductance is in the range between 2 nH and 30 nH, and preferably between 4 nH and 20 nH.

The aforesaid capacitive element (S12, S22), governed by the resonance relation of the system defined as $LC=(\omega^2)^{-1}$ and where $\omega=2\pi f$ and f the working resonance frequency, is a capacitor having a capacitance between 1 pF and 12 pF, preferably between 2 pF and 10 pF.

According to an embodiment of the handpiece 4, the aforesaid handpiece antenna 12 is configured to operate in frequency ranges in the UHF RFID band between 860 MHz and 960 MHz.

According to an implementation option, all the antenna segments are characterized by equal capacitance C and inductance L values.

According to another implementation option, the inductance values L of the radiant metal element are different from segment to segment, and the capacitance values C of the capacitive element are different from segment to segment, depending on the inductance value L of the respective segment.

In accordance with an embodiment, the handpiece assembly 4 further comprises a handpiece identifier 45 adapted to communicate wirelessly or by wire with the aforesaid handpiece antenna 12.

Such a handpiece identifier 45 is configured to provide handpiece antenna identification information and/or information related to operating conditions and/or operating frequencies of the handpiece antenna 12.

In accordance with an embodiment of the handpiece assembly 4, the aforesaid radiofrequency signal supply means comprise a signal guide 50 and a handpiece antenna connection element 28.

The signal guide comprises, according to a preferred embodiment, a microstrip printed circuit of 50-ohm impedance configured to carry a radiofrequency supply signal from a connection cable 34, between the handpiece 4 and a control element 21 of the medical device 20, to the handpiece antenna 12.

According to another embodiment, the signal guide 50 comprises a miniaturized coaxial cable of 50-ohm impedance.

The handpiece antenna connection element 28, connected to said signal guide 50 and the handpiece antenna 12, comprises said first terminal 51 and second terminal 52 of the radiofrequency signal supply means.

According to an embodiment, the aforesaid microstrip circuit is a 50-ohm impedance-controlled circuit, comprising metal tracks less than one millimeter thick.

The aforesaid microstrip circuit can be obtained by means of a multilayer printed circuit based on technologies known per se.

According to a particular implementation option, the aforesaid microstrip circuit comprising metal tracks is between 0.2 mm and 1.0 mm thick, preferably between 0.35 mm and 0.85 mm, and is made of Vetronite material type FR4 or Kapton—Polyamide or Rogers.

In accordance with an embodiment of the handpiece assembly, the aforesaid coil radiating structure of the handpiece antenna has a diameter smaller than 30 mm so as to be contained within an inner wall of the handpiece distal portion 22.

According to an embodiment of the handpiece assembly, the handpiece antenna 12 is connected in either fixed or separable manner to the handpiece distal portion 22.

According to a particular embodiment of the handpiece assembly, the handpiece antenna 12 is made from a T or Γ shaped flexible rigid multilayer printed circuit board, in which the flexible part (e.g., Kapton—polyamide) extends from the rigid part (e.g., Vetronite type FR4 or Rogers).

When the aforesaid flexible rigid multilayer printed circuit board is placed in position inside the cone of the handpiece, the upper part of the T or Γ wraps on the cone of the light guide, causing the edges of the upper part of the T or Γ to overlap, allowing the electrical contact (i.e., forming the loop or the segmented ring), e.g., by soldering or ultrasonic welding.

In this case, exactly in the joining part of the vertical segment of the T or Γ with the horizontal segment, a TAG is placed, electrically connected through a decoupling capacitor. Such a TAG performs the function of the aforesaid handpiece identifier and performs the function of identifying the handpiece antenna cone, e.g., for the purpose of traceability, for verifying correct use relative to the geographical area (for example, according to the continent or country of destination—e.g., Europe, USA or Japan—the need arises to adapt the handpiece antenna to the local working frequency, which can be achieved with a specific set of antenna capacitors with an appropriate value, adapted to the correct working frequency) and for the compatibility of the insert with respect to the clinical application.

With reference to FIGS. 21-24, further information about possible embodiments of the medical device handpiece assembly will be provided below.

Figure 22:
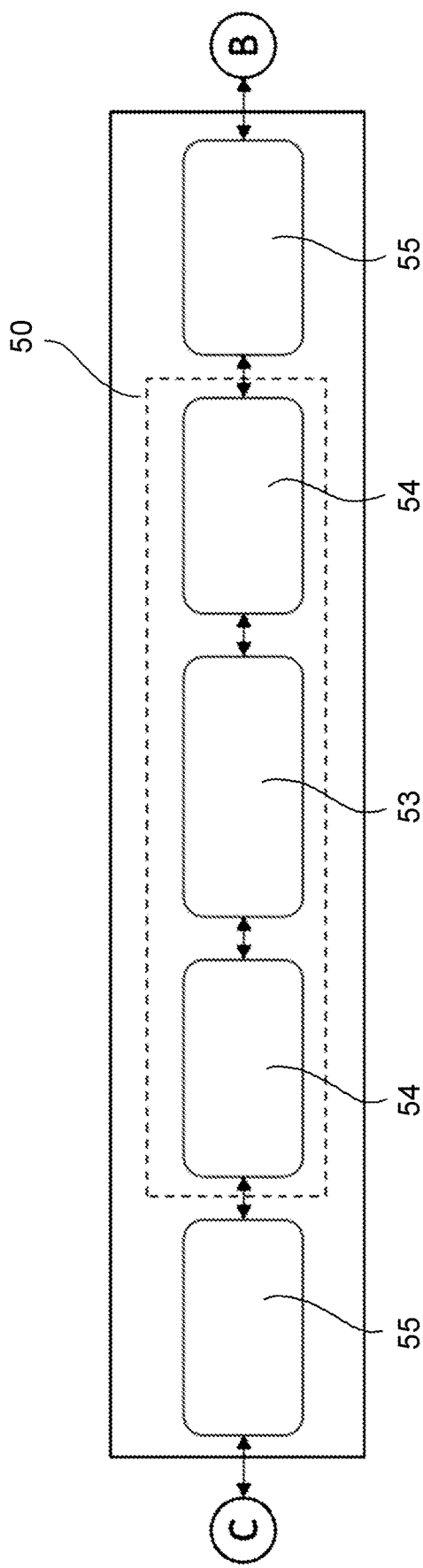
FIG. 22 shows a simplified block diagram of the RF signal distribution mode in the handpiece.
Figure 23:
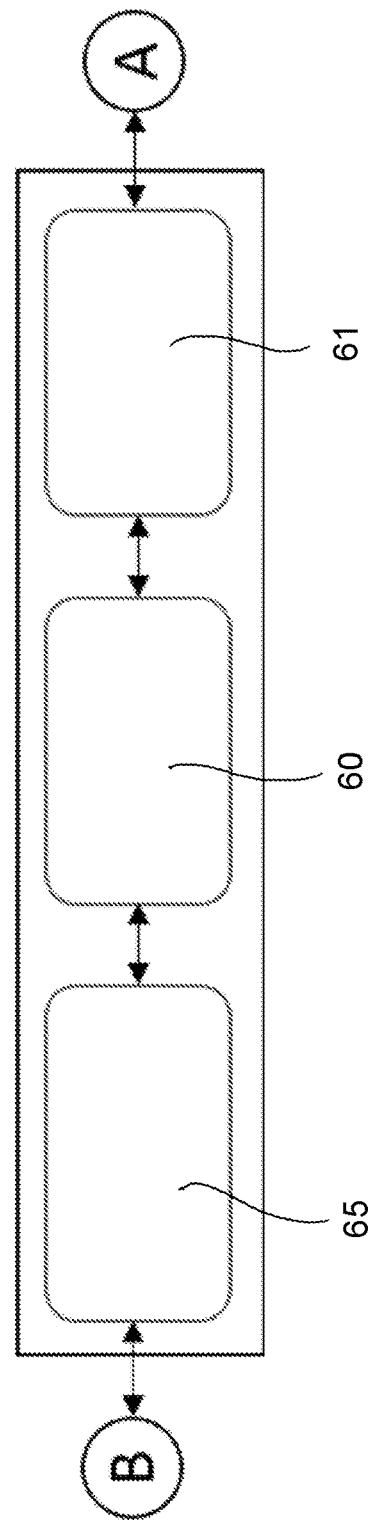
FIG. 23 shows a block diagram of a coaxial cable connection adapted to connect the handpiece and a medical system control unit.

FIG. 22 shows a simplified block diagram of the RF signal distribution mode in the handpiece. In such a block diagram, a microstrip circuit 50 in the aforesaid embodiment is indicated comprising a multilayer flexible circuit, which in turn comprises an impedance-adapted circuit on printed circuit 53 and, at each end of such a circuit 53, a respective RF 54 impedance-adapted network.

In this embodiment, the microstrip circuit 50 has the function of transmitting, with the lowest possible losses, a composite signal, including both the RF signal for the handpiece antenna and the DC signal for the LED lighting circuit of the light cone.

The microstrip or stripline circuit is an established technique in the field of controlled impedance printed circuit boards, in which a high degree of integrity of the high-frequency signals is to be maintained. Additionally, such a microstrip circuit has very small dimensions (in particular, thickness), thus adapting to the small inner space available in the handpiece. For example, the microstrip is adapted to obtain a thickness in the range between 0.2÷1.0 mm, and preferably between 0.35÷0.85 mm.

Upstream of the microstrip circuit (reference point indicated as B in FIGS. 22 and 23) there is a minimum RF area connector 55 with pin connections, configured to connect to a corresponding minimum RF area connector 65 with pin connections interfaced with a coaxial cable 60.

Such a coaxial cable 60 (shown in FIG. 23) connects the handpiece 4 to the control element 21 of the medical device and is used to transmit the RF signals between the handpiece 4 and the control element 21.

Returning to FIG. 22, downstream of the microstrip circuit (reference point indicated as C in FIGS. 22 and 21) there is another minimum RF area connector 55 with pin connections, configured to connect to a corresponding further minimum RF area connector 55 with pin connections interfaced with an RF-DC decoupling network (or decoupler) 56.

Indeed, in this case, in the flexible rigid circuit, an RF-DC decoupler 56 is also obtained (shown in FIG. 21), which separates the RF and DC components, and routes the DC component to the LED lighting circuit 57 of the light cone, and the RF component to the handpiece antenna 12.

The aforesaid minimum area RF connectors 55 with pin connections are configured to minimize the insertion area, such as to minimize the RF radiation losses at the interconnection points, and to allow adequate transmission performance even in a context where the known RF connectors for coaxial cables cannot be used for dimensional reasons.

Figure 21:
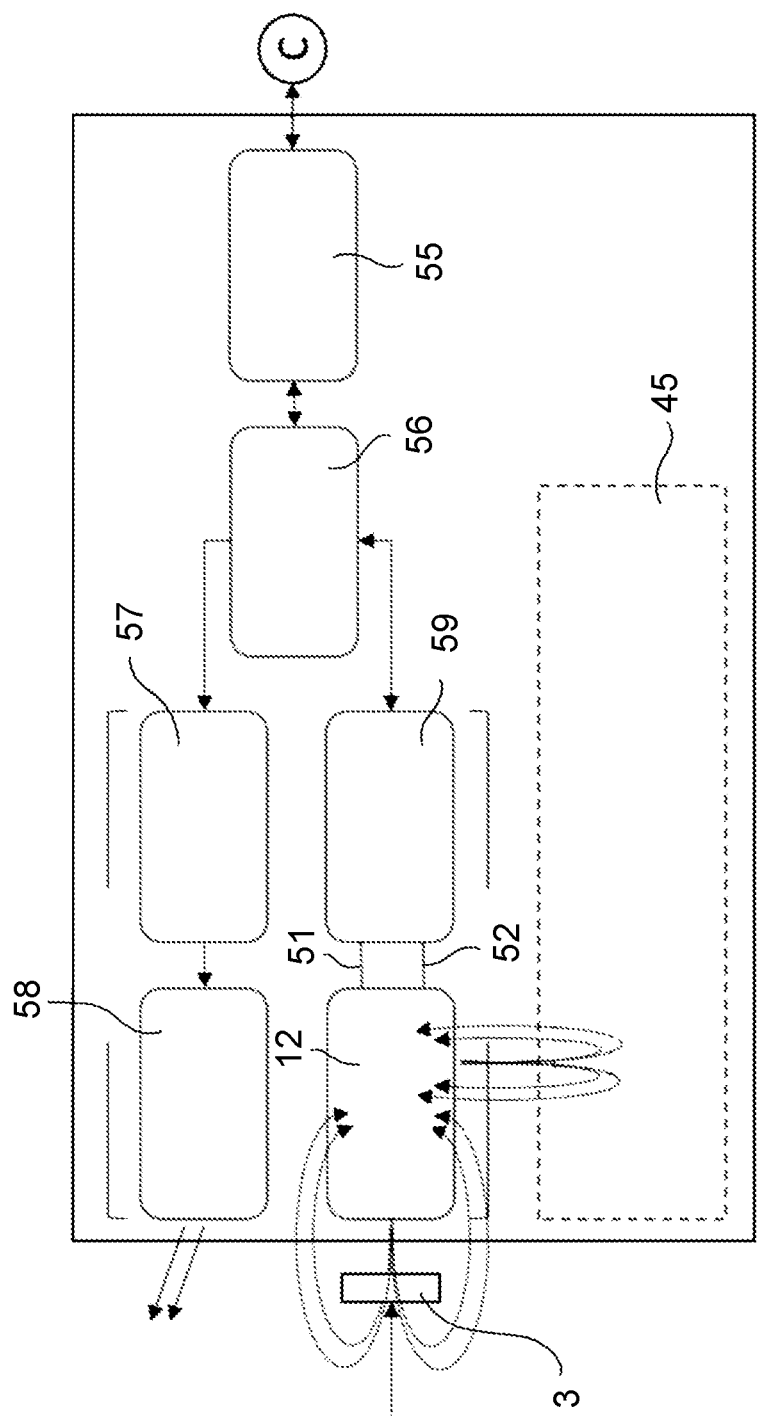
FIG. 21 shows a block diagram of a medical device handpiece portion containing a handpiece antenna.

FIG. 21 also shows the functional blocks corresponding to the lighting circuitry 57 and the light signal guides DC 58, and the handpiece antenna 12, which is a near field antenna with RF input impedance adjustment 59.

FIG. 21 also shows the functional blocks corresponding to the identifier (tag) of the handpiece 45, connected in wireless near field mode or wired mode by means of decoupling capacitor with the handpiece antenna 12.

Figure 24:
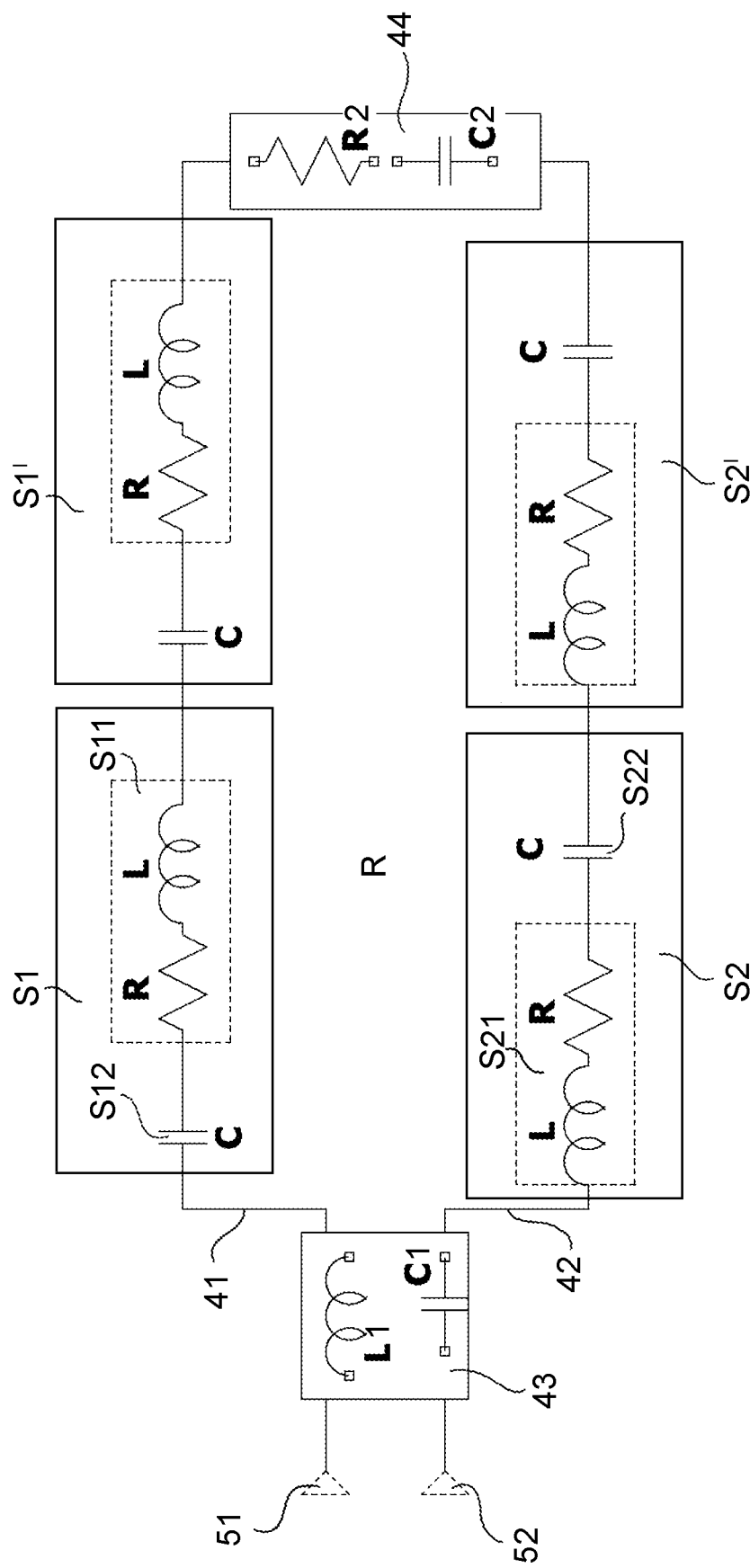
FIG. 24 shows an equivalent circuit of an embodiment of a handpiece antenna.

FIG. 24 shows an equivalent electrical circuit of the handpiece antenna, according to an embodiment.

Hereinafter, a medical device 20 is described comprising a control element 21, a medical device handpiece 4 according to any one of embodiments described above and an insert assembly 1 comprising a radiofrequency identifier 3, an insert antenna 8 and an insert 2 adapted to interact with a part of a patient's body.

The aforesaid insert assembly 1 is operatively and mechanically connected separably from the handpiece 4 of the handpiece assembly.

The aforesaid insert antenna 8 and handpiece antenna 12 are configured to communicate with each other wirelessly in radiofrequency.

In accordance with an embodiment, the medical device 20 is configured in such a way that, when said insert assembly 1 is connected to the handpiece 4, the insert antenna 8 is arranged in the vicinity of the handpiece antenna 4, in the aforesaid insertion region R in which the radiofrequency electromagnetic field generated by the handpiece antenna 4 is present in radiant condition.

As can be noted, the object of the present invention is fully achieved by the system chain (insert assembly 1—handpiece assembly 22;4;24—cable 34—medical device 20—control device 21) developed and described above, by virtue of the structural and functional features thereof.

Indeed, by virtue of the features described in detail above, the insert assembly allows to reduce and minimize undesired phenomena which worsen the communication between the insert assembly and the remaining parts of the medical device.

In particular, from the point of view of the fields, the ferromagnetic layer has the function of isolating the wireless transceiver structure from the metal parts of the insert body, preventing the creation of the reflected antagonist field and thus avoiding the phenomena of attenuation or zeroing of the overall electromagnetic field (complained in the prior art).

The addition of the ferromagnetic layer, with a complex effective magnetic permeability, modifies the magnetic profile by influencing the mutual inductance and self-inductance. By appropriately selecting material and dimensions of the ferromagnetic layer (e.g., as in the abovementioned implementation options) it is possible to have degrees of freedom to optimize the design of the transceiver structure, maximizing the intensity of the overall field present at the antenna, and improving communication as desired.

Ultimately, this leads to an improvement in the patient safety requirement, which is extremely important in the technical and application areas indicated, but in particular in the dental and medical areas defined in the document.

From a "concentrated parameters" electrical point of view, the ferromagnetic layer increases the inductance of the LC system (where C is the chip). This feature, in turn, determines the further effect of lowering the resonance frequency of the "antenna-chip" system, which has the further advantage, and achieves the further desired object, of bringing it within the limits required by the UHF band, and thus facilitating and improving the design of the transceiver structure, making it more easily adapted to the desired uses.

With reference to the requirements for the handpiece antenna, it is worth noting that the handpiece antenna, by virtue of the functional and structural features described above, has very small dimensions (adapted to the context of use), can be easily manufactured and provides adequate transmissive performance.

Indeed, by virtue of the loop or segmented loop structure and the positioning in the distal handpiece portion, around the insertion region of the insert assembly, the handpiece antenna has a uniform emission lobe over the entire emission zone thereof and generates a stable and sufficiently intense electromagnetic field precisely in the insertion region of the insert assembly.

The structure of the segmented ring antenna, comprising line sections connected by capacitors which compensate and/or cancel with the capacitance thereof the inductance of the corresponding copper line segment, avoids the phase inversion of the current which circulates on the coil, thus obtaining a uniform and strong field especially in the center of the coil, in a region in which the insert antenna intended to communicate with the handpiece antenna is positioned, ultimately to allow the unique insert identifier to be read and the operating and maintenance parameters of the insert to be written into or read from the non-volatile memory.

The series configuration of the capacitors connecting the line sections of the segmented ring antenna structure allows an accurate tuning of the resonance frequency, being able to rely on the overall capacitance achieved by a multitude of capacitors ensuring a fine resolution of the total capacitance value rather than a single component with coarse tolerances and nominal values imposed by the market.

Furthermore, the handpiece comprises a communication line (handpiece antenna and related radiofrequency signal supply means) which can allow for adequate impedance adaptation (essential for effective RF signal transmission and emission) even in a small structure, which does not allow the use of common impedance adapted RF transmission methods (e.g., coaxial cables and related RF connectors). Such a purpose is achieved, for example, through an impedance adaptation power supply network, included in the segmented ring structure of the antenna, and by a microstrip RF signal distribution circuit with the features described above.

Those skilled in the art may make changes and adaptations to the embodiments of the insert assembly and the medical system described above or may replace elements with others which are functionally equivalent to meet contingent needs without departing from the scope of the appended claims. All the features described above as belonging to a possible embodiment may be implemented irrespective of the other embodiments described.

LIST OF REFERENCE NUMERALS 1 insert assembly
2 insert
3 radiofrequency identifier
4 medical device handpiece
5 insert metal tang
6 ferromagnetic layer
7 dielectric layer
8 insert antenna
9 insert antenna metal element
10 identification chip
11 transceiver device
12 handpiece antenna
13 chip seat
14 outer side of said substantially planar profile of said metal insert antenna element of said insert antenna
15 inner side of said insert antenna metal element of said insert antenna
16 protruding chip portion
17 inner insulating layer, e.g., double-sided adhesive
18 outer insulating layer, e.g., PVC or PET or polyamide
19 biocompatible protective layer, e.g., paint or mono or multiple-component epoxy compound
20 medical device
21 control element
22 handpiece distal portion
23 handpiece central portion
24 handpiece proximal portion
25 transducer e.g., piezoelectric transducer
26 ultrasound generator or control unit
27 threaded tang for insert attachment
28 handpiece antenna connection element
29 LED
30 handpiece distal end
31 light guide element
32 light concentrator
33 handpiece distal portion lid
34 connection cable
41 handpiece antenna first segment first end
42 handpiece antenna last segment second end
43 handpiece antenna input impedance adaptation first electrical network
44 handpiece antenna impedance adaptation second electrical network
45 handpiece identifier
50 signal guide of the radiofrequency signal supply means (e.g., microstrip circuit)
51 first terminal of the signal supply means
52 second terminal of the signal supply means
53 impedance-adapted circuit on microstrip printed circuit board
54 microstrip circuit RF impedance adaptation network
55 minimum area RF connector with pin connections
56 RF-DC decoupling network (or decoupler)
57 LED lighting circuit
58 guides for the DC light signal
59 handpiece antenna input RF impedance adaptation network
60 coaxial connection cable between handpiece and control unit
61 50-ohm RF coaxial connector
65 minimum area RF connector with pin connections
71 identification chip power management element 71
72 identification chip modulator/demodulator element
73 identification chip controller
74 identification chip non-volatile memory
101 ultrasonic system
102 generator means

The invention claimed is:

1. An insert assembly with radiofrequency identifier, said insert assembly being configured to be inserted in handpiece of a medical device, said insert assembly comprising:
an insert adapted to interact with a part of a patient's body, the insert comprising an insert metal tang;
a ferromagnetic layer, arranged in contact with said insert metal tang of the insert, wherein said ferromagnetic layer comprises ferromagnetic material;
a dielectric layer, arranged in contact with said ferromagnetic layer;
an insert antenna, arranged in contact with said dielectric layer, and comprising an insert antenna metal element extending along a predefined substantially planar profile, said predefined substantially planar profile, as a whole, wraps, at least partially surrounding said insert metal tang, said insert antenna being configured to receive and transmit electromagnetic fields within a given frequency range, modulated or not modulated; and an identification chip, operatively connected to said insert antenna, said identification chip being configured to transmit, when activated, information relating to the insert assembly;

wherein said ferromagnetic layer is adapted to reduce or cancel phenomena of attenuation and/or distortion of an electromagnetic field, caused by field parasitic effects in a vicinity of the insert antenna due to interaction of a transmitted or received electromagnetic field with at least one of metal parts of the insert metal tang, liquids present in the insert, the insert antenna metal element, and wherein said ferromagnetic layer, dielectric layer and insert antenna form a transceiver device configured to put in wireless communication said identification chip with a handpiece antenna of said handpiece.

2. The insert assembly of claim 1, wherein said given frequency range comprises one or more radiofrequency ranges, and wherein said insert antenna is a radio frequency antenna configured to operate at radiofrequency, and wherein said identification chip is an RF identification chip.

3. The insert assembly of claim 1, wherein said dielectric layer is distinct from said ferromagnetic layer and is interposed between said ferromagnetic layer and said insert antenna to electrically isolate said insert antenna metal element with respect to the ferromagnetic material of said ferromagnetic layer.

4. The insert assembly of claim 1, wherein said transceiver device formed by said ferromagnetic layer, dielectric layer and insert antenna is modellable as an electric circuit, and wherein electrical parameters of the electric circuit depend on dimensions and material of the ferromagnetic layer.

5. The insert assembly of claim 4, wherein said transceiver device formed by said ferromagnetic layer, dielectric layer and insert antenna, and the identification chip are modellable as an electric circuit, in which inductance parameters depend on dimensions and material of the ferromagnetic layer, of the dielectric layer and of the insert antenna, and capacitance parameters mainly depend on the identification chip, and wherein the frequency range on which the transceiver device is configured to operate depends on said inductance and capacitance parameters.

6. The insert assembly of claim 2, wherein operating frequency ranges of the transceiver device include frequency ranges in an ultra-high frequency (UHF) radio frequency identification (RFID) band between 860 MHz and 960 MHz.

7. The insert assembly of claim 1, wherein said ferromagnetic layer, dielectric layer and insert antenna form a stack having a thickness comprised between 50 micrometers and 800 micrometers, said stack being adapted to be inserted into an insert having a diameter not exceeding 6,400 micrometers.

8. The insert assembly of claim 1, wherein a thickness of the ferromagnetic layer that is a radial dimension with respect to the insert, is comprised between 20 micrometers and 400 micrometers.

9. The insert assembly of claim 1, wherein said ferromagnetic layer is made of thin, highly permeable sintered ferrite or of a polymeric base, mixed with dispersed micrometric-sized magnetic powders.

10. The insert assembly of claim 1, wherein said ferromagnetic layer, dielectric layer and insert antenna envelope a central metal element forming a substantially concentric structure.

11. The insert assembly of claim 1, wherein said insert antenna is made of aluminum.

12. The insert assembly of claim 1, wherein said insert antenna has a shape of a flat rectangle, wherein a length of a short side of the flat rectangle is between 1 mm and 6 mm, a length of a long side of the flat rectangle is between 10 mm and 30 mm, and thickness of said insert antenna is smaller than 50 micrometers.

13. The insert assembly of claim 1, further comprising a biocompatible protective layer resistant to vibrations and temperature, arranged externally with respect to said ferromagnetic layer, dielectric layer, insert antenna and identification chip, wherein the biocompatible protective layer is a single or multiple component epoxy compound or paint.

14. The insert assembly of claim 1, wherein said ferromagnetic layer is arranged in contact with said insert metal tang by a double-sided adhesive layer.

15. The insert assembly of claim 1, wherein the identification chip is an RFID chip.

16. The insert assembly of claim 1, wherein said identification chip has a parallelepiped shape with dimensions of a base side between 50 micrometers and 1200 micrometers, and thickness less than 300 micrometers.

17. The insert assembly of claim 1, wherein the identification chip is configured to store, and transmit, when excited, through said transceiver device, one or more information selected from:

unique and non-modifiable identification of the insert assembly;

information about traceability of the insert assembly;

information about compatibility with a connected medical device;

information about suitability for use in selected type of device and clinical intervention;

information about operating frequency ranges in which the transceiver device of the insert assembly is configured to operate;

information about integrity of the insert assembly;

information about whether the insert assembly is correctly inserted, when the insert assembly is inserted in a respective handpiece;

information about operating parameters and operating times of the insert assembly;

error or alarm messages in presence of anomalous operating situations; and information about predictive and/or scheduled maintenance.

18. The insert assembly of claim 1, wherein the insert assembly is configured to operate in association with a medical device for dental prophylaxis or implantology and medical applications in maxillofacial, skull facial, neuro-spine and orthopedics fields or other anatomical districts.

19. A medical device comprising a control unit, a handpiece provided with a handpiece antenna and an insert assembly with radiofrequency identifier, said insert assembly being configured to be inserted in the handpiece of the medical device, said insert assembly comprising:

an insert adapted to interact with a part of a patient's body, the insert comprising an insert metal tang;

a ferromagnetic layer arranged in contact with said insert metal tang of the insert, wherein said ferromagnetic layer comprises ferromagnetic material;

a dielectric layer arranged in contact with said ferromagnetic layer;

an insert antenna arranged in contact with said dielectric layer, and comprising an insert antenna metal element extending along a predefined substantially planar profile, said predefined substantially planar profile, as a whole, wraps, at least partially surrounding said insert metal tang, said insert antenna being configured to receive and transmit electromagnetic fields within a given frequency range, modulated or not modulated; and an identification chip operatively connected to said insert antenna, said identification chip being configured to transmit, when activated, information relating to the insert assembly;

wherein said ferromagnetic layer is adapted to reduce or cancel phenomena of attenuation and/or distortion of an electromagnetic field, caused by field parasitic effects in a vicinity of the insert antenna due to interaction of a transmitted or received electromagnetic field with at least one of metal parts of the insert metal tang, liquids present in the insert, the insert antenna metal element, and wherein said ferromagnetic layer, dielectric layer and insert antenna form a transceiver device configured to put in wireless communication said identification chip with the handpiece antenna of said handpiece, said insert assembly being operatively and mechanically connected to said handpiece of the medical device, and wherein said insert antenna is configured to communicate wirelessly with said handpiece antenna.

20. The medical device of claim 19, said medical device being configured to manage and control bidirectional communications with the insert assembly and to store information selected from:

unique and non-modifiable identification of the insert assembly;

information about traceability of the insert assembly;

information about compatibility with a connected medical device;

information about suitability for use in selected type of device and clinical intervention;

information about operating frequency ranges in which the transceiver device of the insert assembly is configured to operate;

information about integrity of the insert assembly;

information about whether the insert assembly is correctly inserted, when the insert assembly is inserted in a respective handpiece;

information about operating parameters and operating times of the insert assembly;

error or alarm messages in presence of anomalous operating situations; and information about predictive and/or scheduled maintenance, and stored in the insert assembly, in a memory of the medical device and, where present, on an external server of the medical device, through Internet of Things (IoT) technology.

\* \* \* \* \*